(12) United States Patent
Anex et al.

(10) Patent No.: US 7,517,440 B2
(45) Date of Patent: Apr. 14, 2009

(54) ELECTROKINETIC DELIVERY SYSTEMS, DEVICES AND METHODS

(75) Inventors: Deon S. Anex, Livermore, CA (US);
Phillip H. Paul, Livermore, CA (US);
David W. Neyer, Castro Valley, CA (US); Edwin J. Hlavka, Palo Alto, CA (US)

(73) Assignee: Eksigent Technologies LLC, Dublin, CA (US)

( * ) Notice: Subject to any disclaimer, the term of this patent is extended or adjusted under 35 U.S.C. 154(b) by 448 days.

(21) Appl. No.: 11/112,867

(22) Filed: Apr. 21, 2005

(65) Prior Publication Data
US 2005/0247558 A1    Nov. 10, 2005

Related U.S. Application Data

(63) Continuation-in-part of application No. PCT/US03/32895, filed on Oct. 17, 2003, and a continuation-in-part of application No. 10/322,083, filed on Dec. 17, 2002, now Pat. No. 7,267,753, and a continuation-in-part of application No. 10/273,723, filed on Oct. 18, 2002, now Pat. No. 7,235,164, and a continuation-in-part of application No. 10/198,223, filed on Jul. 17, 2002, now Pat. No. 7,364,647.

(60) Provisional application No. 60/564,497, filed on Apr. 21, 2004.

(51) Int. Cl.
*B01D 57/02* (2006.01)
*B01D 59/42* (2006.01)
*C25B 9/12* (2006.01)
*C25B 15/04* (2006.01)

(52) U.S. Cl. .................. 204/450; 204/263; 204/265; 204/266; 204/600; 417/48; 137/1; 137/8; 137/10; 137/12; 137/825

(58) Field of Classification Search ................. 204/450, 204/600, 263, 265, 266; 417/48; 137/1, 137/8, 10, 12, 825
See application file for complete search history.

(56) References Cited

U.S. PATENT DOCUMENTS

2,615,940 A    10/1952    Williams
(Continued)

FOREIGN PATENT DOCUMENTS

CN    2286429 Y    7/1998
(Continued)

OTHER PUBLICATIONS

Adamson, A.W. et al., "Physical Chemistry of Surfaces," Sixth Ed., 1997, pp. 185-187, Wiley, NY.
(Continued)

*Primary Examiner*—Bruce F Bell
(74) *Attorney, Agent, or Firm*—Sheldon Mak Rose & Anderson

(57) ABSTRACT

A method of pumping fluid including the steps of providing an electrokinetic pump comprising a pair of double-layer capacitive electrodes having a capacitance of at least $10^{-2}$ Farads/cm$^2$ and being connectable to a power source, a porous dielectric material disposed between the electrodes and a reservoir containing pump fluid; connecting the electrodes to a power source; and moving pump fluid out of the reservoir substantially without the occurrence of Faradaic processes in the pump. The invention also includes an electrokinetic pump system having a pair of double-layer capacitive electrodes having a capacitance of at least $10^{-2}$ Farads/cm$^2$; a porous dielectric material disposed between the electrodes; a reservoir containing pump fluid; and a power source connected to the electrodes; the electrodes, dielectric material and power source being adapted to move the pump fluid out of the reservoir substantially without the occurrence of Faradaic processes in the pump.

103 Claims, 12 Drawing Sheets

U.S. PATENT DOCUMENTS

| | | | |
|---|---|---|---|
| 2,644,900 A | 7/1953 | Hardway, Jr. | |
| 2,644,902 A | 7/1953 | Hardway, Jr. | |
| 2,661,430 A | 12/1953 | Hardway, Jr. | |
| 2,995,714 A | 8/1961 | Hannah | |
| 3,143,691 A | 8/1964 | Hurd | |
| 3,209,255 A | 9/1965 | Estes et al. | |
| 3,298,789 A | 1/1967 | Mast et al. | |
| 3,427,978 A | 2/1969 | Hanneman et al. | |
| 3,544,237 A | 12/1970 | Walz | |
| 3,630,957 A | 12/1971 | Rey et al. | |
| 3,682,239 A | 8/1972 | Abu-Romia | |
| 3,923,426 A | 12/1975 | Theeuwes et al. | |
| 4,383,265 A | 5/1983 | Kohashi | |
| 4,396,925 A | 8/1983 | Kohashi | |
| 4,402,817 A | 9/1983 | Maget | |
| 4,999,069 A | 3/1991 | Brackett et al. | |
| 5,037,457 A | 8/1991 | Goldsmith et al. | |
| 5,041,181 A | 8/1991 | Brackett et al. | |
| 5,087,338 A | 2/1992 | Perry et al. | |
| 5,126,022 A | 6/1992 | Soane et al. | |
| 5,534,328 A | 7/1996 | Ashmead et al. | |
| 5,573,651 A | 11/1996 | Dasgupta et al. | |
| 5,581,438 A | 12/1996 | Halliop | |
| 5,683,443 A | 11/1997 | Munshi et al. | |
| 5,858,193 A | 1/1999 | Zanzucchi et al. | |
| 5,888,390 A | 3/1999 | Craig | |
| 5,942,093 A | 8/1999 | Rakestraw et al. | |
| 5,958,203 A | 9/1999 | Parce et al. | |
| RE36,350 E | 10/1999 | Swedberg et al. | |
| 5,961,800 A | 10/1999 | McBride et al. | |
| 5,964,997 A | 10/1999 | McBride | |
| 5,989,402 A | 11/1999 | Chow et al. | |
| 5,997,708 A | 12/1999 | Craig | |
| 6,007,690 A | 12/1999 | Nelson et al. | |
| 6,012,902 A | 1/2000 | Parce | |
| 6,013,164 A | 1/2000 | Paul et al. | |
| 6,019,882 A | 2/2000 | Paul et al. | |
| 6,054,034 A | 4/2000 | Soane et al. | |
| 6,068,243 A | 5/2000 | Hoggan | |
| 6,068,767 A | 5/2000 | Garguilo et al. | |
| 6,074,725 A | 6/2000 | Kennedy | |
| 6,080,295 A | 6/2000 | Parce et al. | |
| 6,086,243 A | 7/2000 | Paul et al. | |
| 6,100,107 A | 8/2000 | Lei et al. | |
| 6,106,685 A | 8/2000 | McBride et al. | |
| 6,126,723 A | 10/2000 | Drost et al. | |
| 6,129,973 A | 10/2000 | Martin et al. | |
| 6,156,273 A | 12/2000 | Regnier et al. | |
| 6,171,067 B1 | 1/2001 | Parce | |
| 6,176,962 B1 | 1/2001 | Soane et al. | |
| 6,210,986 B1 | 4/2001 | Arnold et al. | |
| 6,224,728 B1 | 5/2001 | Oborny et al. | |
| 6,255,551 B1 | 7/2001 | Shapiro et al. | |
| 6,267,858 B1 | 7/2001 | Parce et al. | |
| 6,277,257 B1 | 8/2001 | Paul et al. | |
| 6,287,440 B1 | 9/2001 | Arnold et al. | |
| 6,290,909 B1 | 9/2001 | Paul et al. | |
| 6,320,160 B1 | 11/2001 | Eidsnes et al. | |
| 6,344,145 B1 | 2/2002 | Garguilo et al. | |
| 6,352,577 B1 | 3/2002 | Martin et al. | |
| 6,406,605 B1 | 6/2002 | Moles | |
| 6,409,698 B1 | 6/2002 | Robinson et al. | |
| 6,418,968 B1 | 7/2002 | Pezzuto et al. | |
| 6,444,150 B1 | 9/2002 | Arnold | |
| 6,460,420 B1 | 10/2002 | Paul et al. | |
| 6,472,443 B1 | 10/2002 | Shepodd | |
| 6,477,410 B1 | 11/2002 | Henley et al. | |
| 6,495,015 B1 | 12/2002 | Schoeniger et al. | |
| 6,529,377 B1 | 3/2003 | Nelson et al. | |
| 6,689,373 B2 | 2/2004 | Johnson et al. | |
| 6,719,535 B2 | 4/2004 | Rakestraw et al. | |
| 6,729,352 B2 | 5/2004 | O'Connor et al. | |
| 6,755,211 B1 | 6/2004 | O'Connor et al. | |
| 6,770,182 B1 | 8/2004 | Griffiths et al. | |
| 6,814,859 B2 | 11/2004 | Koehler et al. | |
| 7,235,164 B2* | 6/2007 | Anex et al. | 204/600 |
| 7,267,753 B2* | 9/2007 | Anex et al. | 204/600 |
| 2001/0008212 A1 | 7/2001 | Shepodd et al. | |
| 2002/0048425 A1* | 4/2002 | McBride et al. | 385/16 |
| 2002/0056639 A1 | 5/2002 | Lackritz et al. | |
| 2002/0059869 A1 | 5/2002 | Martin et al. | |
| 2002/0066639 A1 | 6/2002 | Taylor et al. | |
| 2002/0070116 A1 | 6/2002 | Ohkawa | |
| 2002/0089807 A1 | 7/2002 | Bluvstein et al. | |
| 2002/0125134 A1 | 9/2002 | Santiago et al. | |
| 2002/0166592 A1 | 11/2002 | Liu et al. | |
| 2002/0185184 A1 | 12/2002 | O'Connor et al. | |
| 2002/0187074 A1 | 12/2002 | O'Connor et al. | |
| 2002/0187557 A1 | 12/2002 | Hobbs et al. | |
| 2002/0189947 A1* | 12/2002 | Paul et al. | 204/461 |
| 2002/0195344 A1* | 12/2002 | Neyer et al. | 204/600 |
| 2003/0052007 A1 | 3/2003 | Paul et al. | |
| 2003/0061687 A1 | 4/2003 | Hansen et al. | |
| 2003/0116738 A1 | 6/2003 | O'Connor et al. | |
| 2003/0143081 A1 | 7/2003 | Rakestraw et al. | |
| 2003/0150792 A1 | 8/2003 | Kochler et al. | |
| 2003/0198130 A1 | 10/2003 | Karp et al. | |
| 2003/0198576 A1 | 10/2003 | Coyne et al. | |
| 2003/0206806 A1 | 11/2003 | Paul et al. | |
| 2003/0226754 A1 | 12/2003 | Le Febre | |
| 2004/0011648 A1 | 1/2004 | Paul et al. | |
| 2004/0074768 A1 | 4/2004 | Annex et al. | |
| 2004/0074784 A1 | 4/2004 | Anex et al. | |
| 2004/0087033 A1 | 5/2004 | Schembri | |
| 2004/0101421 A1 | 5/2004 | Kenny et al. | |
| 2004/0115731 A1 | 6/2004 | Hansen et al. | |
| 2004/0118189 A1 | 6/2004 | Karp et al. | |
| 2004/0129568 A1 | 7/2004 | Seul et al. | |
| 2004/0163957 A1* | 8/2004 | Neyer et al. | 204/450 |
| 2004/0182709 A1 | 9/2004 | Griffiths et al. | |
| 2004/0238052 A1 | 12/2004 | Karp et al. | |
| 2004/0241004 A1 | 12/2004 | Goodson et al. | |
| 2004/0241006 A1 | 12/2004 | Taboryski et al. | |
| 2004/0247450 A1 | 12/2004 | Kutchinsky et al. | |
| 2005/0247558 A1 | 11/2005 | Annex et al. | |

FOREIGN PATENT DOCUMENTS

| | | | |
|---|---|---|---|
| EP | 0421234 | A2 | 4/1991 |
| EP | 1063204 | A2 | 12/2000 |
| JP | 3087659 | | 4/1991 |
| WO | 9639252 | A1 | 12/1996 |
| WO | 9916162 | A1 | 4/1999 |
| WO | 0004832 | A1 | 2/2000 |
| WO | 0055502 | A1 | 9/2000 |
| WO | 0079131 | A1 | 12/2000 |
| WO | 0125138 | A1 | 4/2001 |
| WO | 02068821 | A2 | 9/2002 |
| WO | 02086332 | A1 | 10/2002 |
| WO | 2004007348 | A1 | 1/2004 |
| WO | 2004027535 | A1 | 4/2004 |

OTHER PUBLICATIONS

Ananthakrishnan, V. et al., "Laminar Dispersion in Capillaries: Part I. Mathematical Analysis," A.I.Ch.E. Journal, Nov. 1965, vol. 11(6):1063-1072.

Aris, R., "On the dispersion of a solute in a fluid flowing through a tube," Oxidation Of Organic Sulphides, VI, Proc. Roy. Soc., London, vol. 235A:67-77.

Burgreen, D. et al., "Electrokinetic Flow in Ultrafine Capillary Slits," The Journal of Physical Chemistry, May 1964, vol. 68(5):1084-1091.

Chatwin, P.C. et al., "The effect of aspect ratio on longitudinal diffusivity in rectangular channels," J. Fluid Mech. 1982, vol. 120:347-358.

Doshi, M.R. et al., "Three Dimensional Laminar Dispersion In Open And Closed Rectangular Conduits," Chemical Engineering Science, 1978, vol. 33, pp. 795-804.

Drott, J. et al., "Porous silicon as the carrier matrix in microstructured enzyme reactors yielding high enzyme activities," J. Micromech. Microeng., 1997, vol. 7, pp. 14-23.

Gan, W. et al., "Mechanism of porous core electroosmotic pump flow injection system and its application to determination of chromium(VI) in waste-water," Talanta, 2000, vol. 51, pp. 667-675.

Jessensky, O. et al., "Self-Organized Formation of Hexagonal Pore Structures in Anodic Alumina," J. Electrochem. Soc., Nov. 1998, vol. 145(11), pp. 3735-3740.

Johnson, D.L. et al., "Dependence of the conductivity of a porous medium on electrolyte conductivity," Physical Review Letters, Mar. 1, 1988, vol. 37(7), pp. 3502-3510.

Johnson, D.L. et al., "New Pore-Size Parameter Characterizing Transport in Porous Media," Physical Review Letters, Nov. 17, 1986, vol. 57(20), pp. 2564-2567.

Johnson, D.L. et al., "Theory of dynamic permeability and tortuosity in fluid-saturated porous media," J. Fluid. Mech., 1987, vol. 176, pp. 379-402.

Kobatake, Y. et al., "Flows Through Charged Membranes, I. Flip-Flop Current vs. Voltage Relation," J. Chem. Phys.. Apr. 15, 1964, vol. 40(8), pp. 2212-2218.

Kobatake, Y. et al., Flows Through Charged Membranes, II. Oscillation Phenomena, J. Chem. Phys., Apr. 15, 1964, vol. 40(8), pp. 2219-2222.

Ma, Y. et al., "A review of zeolite-like porous materials," Microporous and Mesoporous Materials, 2000, vol. 37, pp. 243-252.

Morrison, F.A. et al., "Electrokinetic Energy Conversion in Ultrafine Capillaries," Sep. 15, 1965, vol. 43(6), pp. 2111-2115.

Nakanishi, K. et al., "Phase separation in silica sol-gel system containing polyacrylic acid," Journal of Non-Crystalline Solids, 1992, vol. 139, pp. 1-13.

Paul, P.H. et al., "Electrokinetic Pump Application in Micro-Total Analysis Systems," Micro Total Analysis Systems 2000, Kluwer Academic Publishers, 2000, pp. 583-590.

Paul, P.H. et al., "Electrokinetic Generation of High Pressures Using Porous Microstructures," Micro Total Analysis Systems '98, 1998, Kluwer Academic Publishers, pp. 49-52.

Peters, E.C. et al., "Molded Rigid Polymer Monoliths as Separation Media for Capillary Electrochromatography," Anal. Chem. 1997, vol. 69, pp. 3646-3649.

Philipse, A.P., "Solid opaline packings of colloidal silica spheres," Journal of Materials Science Letters, 1989, vol. 8, pp. 1371-1373.

Rastogi, R.P., "Irreversible Thermodynamics of Electro-osmotic Effects," J. Scient. Ind. Res., Aug. 1969, vol. 28, pp. 284-292.

Rice, C.L. et al., "Electrokinetic Flow in a Narrow Cylindrical Capillary," J. Phys. Chem., Nov. 1965, vol. 69(11), pp. 4017-4023.

Rosen, M.J., "Adsorption of Surface-Active Agents at Interfaces: The Electrical Double Layer," Surfactants and Interfacial Phenomena, Second Ed., John Wiley & Sons, pp. 33-107.

Conway, B.E., "Electrochemical Supercapacitors Scientific Fundamentals and Technological Applications," Kluwer Academic/Plenum Publishers, 1999, pp. 12-13, 104-105, 192-195.

Conway, B.E., "Electrochemical Capacitors Their Nature, Function, and Applications," Electrochemistry Encyclopedia, 2003. Available at http://electrochem.cwru.edu/ed/encycl/art-c03-elchem-cap.htm, accessed May 16, 2006, 14 pages.

Gleiter, H. et al., "Nanocrystalline Materials: A Way to Solids With Tunable Electronic Structures And Properties?," Acta Mater, 2001, vol. 49, pp. 737-745.

Gritsch, S. et al., "Impedance Spectroscopy of Porin and Gramicidin Pores Reconstituted into Supported Lipid Bilayers on Indium—Tin-Oxide Electrodes," Langmuir, 1998, vol. 14, pp. 3118-3125.

Kotz, R. et al., Principles and applications of electrochemical capacitors, Electrochimica Acta, 2000, vol. 45, pp. 2483-2498.

Schmid, G., "Electrochemistry of capillary systems with narrow pores. II. Electroosmosis," J. Membrane Sci., 1998, vol. 150, pp. 159-170.

Schmid, G. et al., "Electrochemistry of capillary systems with narrow pores. V. Streaming potential: Donnan hindrance of electrolyte transport," J. of Membrane Sci., 1998, vol. 150, pp. 197-209.

Taylor, G., "Dispersion of soluble matter in solvent flowing slowly through a tube," Prox. Roy. Soc. (London), vol. 21, pp. 186-203.

Uhlig, E.L.P. et al., "The electro-osmotic actuation of implantable insulin micropumps," Journal of Biomedical Materials Research, 1983, vol. 17, pp. 931-943.

Weston, A. et al., "HPLC and CE Principles and Practice," Academic Press, pp. 82-85.

Wijnhoven, J. et al., "Preparation of Photonic Crystals Made of Air Spheres in Titania," Science, Aug. 7, 1998, vol. 281, pp. 802-804.

Yazawa, T., "Present Status and Future Potential of Preparation of Porous Glass and its Application," Key Engineering Materials, 1996, vol. 115, pp. 125-146.

Office Action for U.S. Appl. No. 10/273,723, mailed Jun. 30, 2004, 12 pages.

Office Action for U.S. Appl. No. 10/273,723, mailed Mar. 22, 2005, 16 pages.

Office Action for U.S. Appl. No. 10/273,723, mailed Sep. 15, 2005, 8 pages.

Office Action for U.S. Appl. No. 10/273,723, mailed Mar. 7, 2006, 8 pages.

Office Action for U.S. Appl. No. 10/273,723, mailed Nov. 15, 2006.

Notice of Allowance for U.S. Appl. No. 10/273,723, mailed Feb. 16, 2007, 8 pages.

Baquiran, et al, "Lippincott's Cancer Chemotherapy Handbook," Second Edition, Lippincott, Philadelphia, 2001.

Becker, et al., "Polymer Microfabrication Methods for Microfluidic Analytical Applications," Electrophoresis, 2000, vol. 21, pp. 12-26.

Belfer, et al., "Surface Modification of Commercial Polyamide Reverse Osmosis Membranes," J. Membrane Sci., 1988, vol. 139, pp. 175-181.

Chu, et al., "Physicians Cancer Chemotherapy Drug Manual," Jones and Barlett Publisher, Massachusetts, 2002.

Churchill, et al., "Complex Variables and Applications," McGraw-Hill, Inc., New York, 1990.

Gennaro, A.R., "Remington: The Science and Practice of Pharmacy," 20th Edition, Lippincott, Williams & Wilkins, Philadelphia, 2000.

Gongora-Rubio, et al., "The Utilization of Low Temperature Co-Fired Ceramics (LTCC-ML) Technology for Meso-Scale EMS, a Simple Thermistor Based Flow Sensor," Sensors and Actuators, 1999, vol. 73, No. 3, pp. 215-221.

Goodman and Gilman's "The Pharmacological Basis of Therapeutics," 10th Edition, McGraw Hill Medical Publishing Division, 2001.

Haisma, J., "Direct Bonding in Patent Literature," Philips J. Res., 1995, vol. 49, pp. 165-170.

Jackson, J.D., "Classical Electrodynamics," 2nd Edition, John Wiley & Sons, Inc., New York, 1962.

Jimbo, et al., "Surface Characterization of Polyacrylonitrile Membranes: Graft-Polymerized with Ionic Monomers as Revealed by Zeta Potential Measurements," Macromolecules, 1998, vol. 31, pp. 1277-1284.

Klein, E., "Affinity Membranes: a 10 Year Review," J. Membrane Sci., 2000, vol. 179, pp. 1-27.

Martin, et al., "Laminated Plastic Microfluidic Components for Biological and Chemical Systems," J. Vac. Sci. Technol., 1999, vol. 17, pp. 2264-2269.

Mroz, et al., "Disposable Reference Electrode," Analyst, 1998, vol. 123, pp. 1373-1376.

Roberts, et al., "UV Laser Machined Polymer Substrates for the Development of Microdiagnostic Systems," Anal. Chem., 1997, vol. 69, pp. 2035-3042.

Skeel, R., "Handbook of Cancer Chemotherapy," 6th Edition, Lippincott Williams & Wilkins, 2003.

Stokes, V.K., "Joining Methods for Plastics and Plastic Composites: An Overview," Poly. Eng. And Sci., 1989, vol. 29, pp. 1310-1324.

Takata, et al., "Modification of transport properties of ion exchange membranes XIV. Effect of molecular weight of polyethyleneimine bonded to the surface of cation exchange membranes by acid-amide bonding on electrochemical properties of the membranes," J. Membrance Sci., 2000, vol. 179, pp. 101-107.

Vinson, J.R., "Adhesive Bonding for Polymer Composites," Polymer Eng. And Science, 1989, vol. 29, pp. 1325-1331.

Watson, et al., "Recent Developments in Hot Plate Welding of Thermoplastics," Poly. Eng. And Sci., 1989, vol. 29, pp. 1382-1386.

* cited by examiner

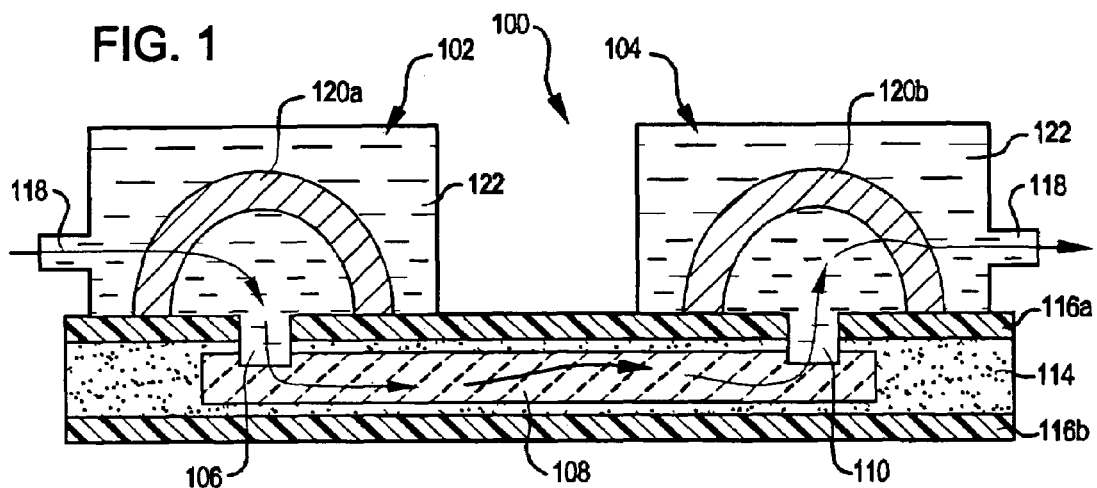
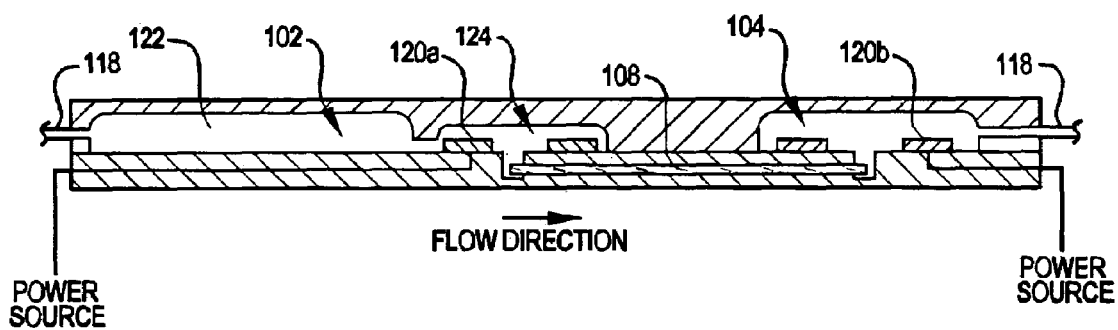
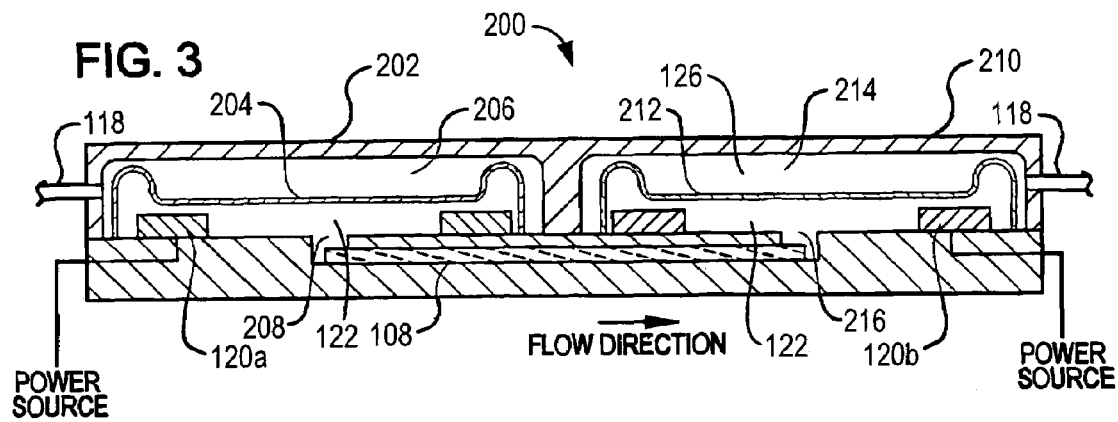

START

MIDPOINT

END OF DELIVERY

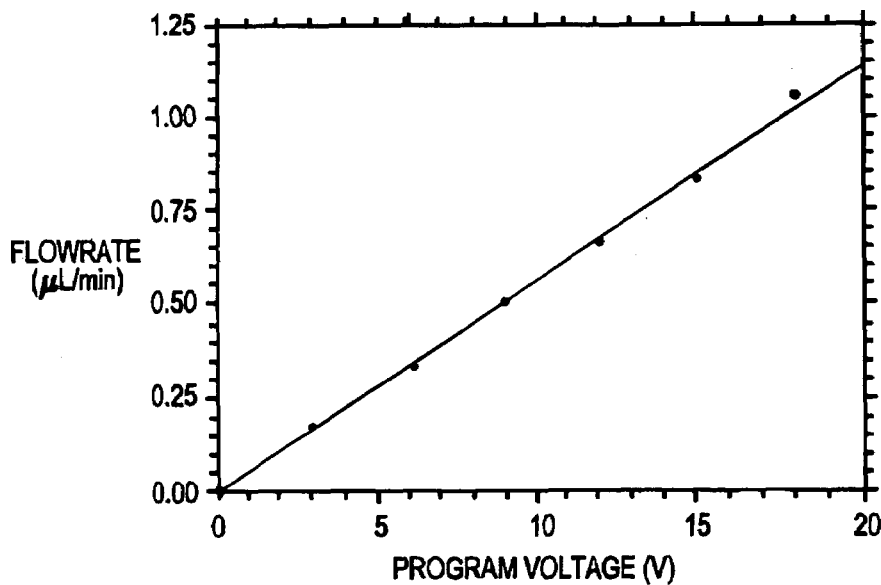
FIG. 9 PERFORMANCE OF A 1 μL/min EK PUMP: VOLTAGE PROGRAMMING OF FLOW RATE
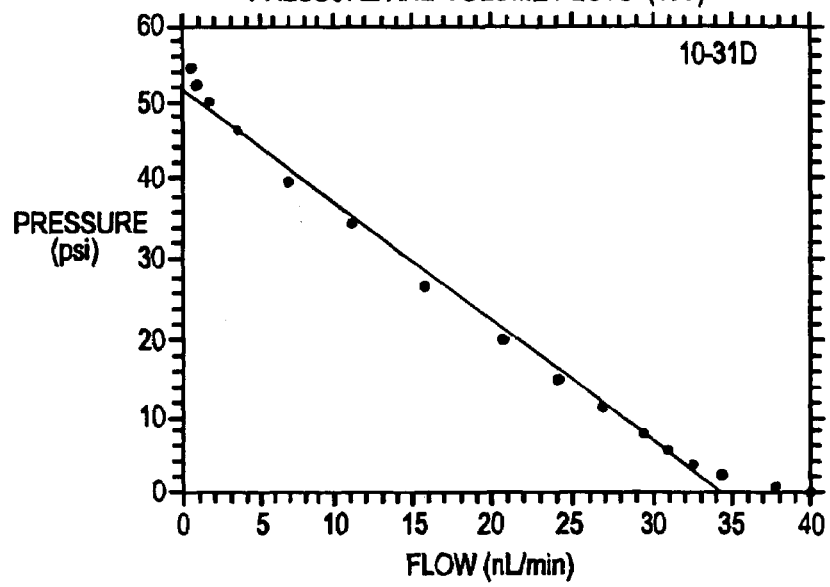
FIG. 10 PUMP CURVE DERIVED FROM PRESSURE AND VOLUME PLOTS (19V)
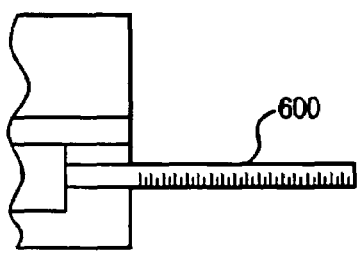
FIG. 11a
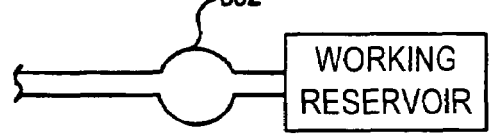
FIG. 11b

ELECTROKINETIC DELIVERY SYSTEMS, DEVICES AND METHODS

CROSS-REFERENCE

This application is a continuation-in-part application of application Ser. No 10/273,723, filed Oct. 18, 2002 now U.S. Pat. No. 7,235,164; application Ser. No. 10/322,083, filed Dec. 17, 2002 now U.S. Pat. No. 7,267,753; application Ser. No. 10/198,223, filed Jul. 17, 2002 now U.S. Pat. No. 7,364,647; and PCT application PCT/US2003/032895, filed Oct. 17, 2003, which are incorporated herein by reference in their entirety and to which we claim priority under 35 USC § 120. This application also claims benefit under 35 USC § 119 of Appl. Ser. No. 60/564,497, filed Apr. 21, 2004, which is also incorporated herein by reference in its entirety.

BACKGROUND OF THE INVENTION

In many diagnostic and therapeutic medical applications (including drug delivery and analyte sampling/monitoring), precise transport of a drug, blood and/or other bio-fluid is important. However, with most conventional diagnostic and therapeutic medical systems, precise movement of large and small aqueous volumes of drugs and other bio-fluids is difficult to achieve. This difficulty arises because conventional systems employ mechanical components to effect fluid transport and delivery. Re-configuration of these systems, to enable highly precise movement of small and large aqueous volumes of a solution containing biomaterials, would be impractical, as the complexity of such systems would make their manufacture expensive, time consuming and labor intensive.

Presently, electrokinetic ("EK") or electro-osmotic manipulations of fluids represent the state-of-the art in controlled, high precision, small volume fluid transport and handling. Electro-osmosis involves the application of an electric potential to an electrolyte, in contact with a dielectric surface, to produce a net flow of the electrolyte.

While electro-osmosis has found widespread and wide ranging applications in chemical analysis (e.g., high-speed liquid chromatography and other chemical separation procedures), its medical applications, such as for drug delivery and analyte sampling, have been limited, despite its advantages over conventional, mechanical approaches. Design challenges, including gas generation in the EK pump fluid, insufficient hydraulic pressure generation, and chemical degradation of the transported material caused by an applied electrical field, need to be overcome. When configured for non-medical use, these drawbacks do not pose major issues because the consequences are minimal, unlike in medical applications.

Accordingly, the present invention is directed to low-cost, high precision, reliable and compact EK pumps and systems adapted for medical applications, including, but not limited to, drug delivery and/or analyte sampling.

SUMMARY OF THE INVENTION

Generally, the present invention contemplates the use of controlled electrokinetic fluid flow techniques for efficient, reliable and highly precise movement of a pump fluid. In addition, various low-cost, precise, reliable and compact medical systems and device for drug delivery and analyte sampling are provided.

One aspect of the invention provides a method of pumping fluid including the steps of providing an electrokinetic pump comprising a pair of double-layer capacitive electrodes having a capacitance of at least $10^{-2}$ Farads/cm$^2$ and being connectable to a power source, a porous dielectric material disposed between the electrodes and a reservoir containing pump fluid; connecting the electrodes to a power source; and moving pump fluid out of the reservoir substantially without the occurrence of Faradaic processes in the pump. The electrodes may be high microscopic surface area electrodes. The moving step may further include moving the pump fluid out of the reservoir and through a pump outlet. In some embodiments, wherein the reservoir is a first reservoir, the electrokinetic pump further comprising a second reservoir, the moving step including moving the pump fluid out of the first reservoir into the second reservoir.

In some embodiments the electrokinetic pump further includes a third reservoir and a sampled fluid disposed in the third reservoir, the moving step further including moving sampled fluid through a pump inlet into the third reservoir as the pump fluid moves from the first reservoir into the second reservoir.

In some embodiments the invention includes a third reservoir and a dispensed fluid disposed in the third reservoir, the moving step further comprising moving dispensed fluid out of the third reservoir and through a pump outlet as the pump fluid moves from the first reservoir into the second reservoir. In some embodiments, the step of moving the pump fluid includes moving the pump fluid at a pump fluid flow rate and the step of moving the dispensed fluid includes moving the dispensed fluid at a dispensed fluid flow rate, the dispensed fluid flow rate being between about 0.1 times and 10 times the pump fluid flow rate. In some embodiments, the providing step includes providing an electrokinetic pump having a volume no greater than 250% of an initial volume of dispensed fluid.

In some embodiments, the third reservoir includes a syringe, and the moving step further includes moving the dispensed fluid out of the syringe and into a patient as the pump fluid moves from the first reservoir into the second reservoir. The method may include adding dispensed fluid to the syringe prior to the moving step.

In embodiments in which the third reservoir includes a collapsible container, the moving step further includes moving the dispensed fluid out of the collapsible container and into a patient as the pump fluid moves from the first reservoir into the second reservoir.

In embodiments wherein the electrokinetic pump includes a first electrokinetic pump and the moving step includes moving dispensed fluid into a patient, the method further includes: providing a second electrokinetic pump includes a pair of double-layer capacitive electrodes connectable to a power source, a porous dielectric material disposed between the electrodes, a first reservoir of pump fluid, a second reservoir, a third reservoir and a dispensed fluid disposed in the third reservoir; connecting the electrodes of the second electrokinetic pump to a power source; moving dispensed fluid out of the third reservoir and through a second electrokinetic pump outlet into the patient as pump fluid of the second electrokinetic pump moves from the first reservoir into the second reservoir of the second electrokinetic pump substantially without the occurrence of Faradaic processes in the second pump. The step of moving dispensed fluid from the first electrokinetic pump may be performed at a first rate and the step of moving dispensed fluid from the second electrokinetic pump is performed at a second rate different than the first rate. The dispensed fluid of the first electrokinetic pump and the dispensed fluid of the second electrokinetic pump are the same kind of fluid or different fluids.

In some embodiments the electrokinetic pump includes a first electrokinetic pump and the moving step includes moving dispensed fluid into a patient, and the method further includes: providing a second electrokinetic pump includes a pair of double-layer capacitive electrodes connectable to a power source, a porous dielectric material disposed between the electrodes, a first reservoir of pump fluid, a second reservoir, a third reservoir and a dispensed fluid disposed in the third reservoir; connecting the electrodes of the second electrokinetic pump to a power source; moving dispensed fluid out of the second electrokinetic pump third reservoir and through the pump outlet into the patient as pump fluid of the second electrokinetic pump moves from the first reservoir into the second reservoir of the second electrokinetic pump substantially without the occurrence of Faradaic processes in the second pump. The step of moving dispensed fluid from the first electrokinetic pump may be performed at a first rate and the step of moving dispensed fluid from the second electrokinetic pump is performed at a second rate different than the first rate. The dispensed fluid of the first electrokinetic pump and the dispensed fluid of the second electrokinetic pump are the same kind of fluid or different fluids.

In embodiments in which the electrokinetic pump includes a first electrokinetic pump and the moving step includes moving dispensed fluid into a patient, the method may further include: providing a second electrokinetic pump includes a pair of double-layer capacitive electrodes connectable to a power source, a porous dielectric material disposed between the electrodes, a first reservoir of pump fluid and a second reservoir; connecting the electrodes of the second electrokinetic pump to a power source; moving dispensed fluid out of the third reservoir and through the pump outlet into the patient as pump fluid of the second electrokinetic pump moves from the first reservoir into the second reservoir of the second electrokinetic pump substantially without the occurrence of Faradaic processes in the second pump.

In some embodiments, the method further includes determining a patient's need for the dispensed fluid, the moving step further including dispensing a quantity of the dispensed fluid in response to the determined need. When, e.g., the dispensed fluid is insulin and the determining step includes determining the patient's blood glucose concentration, the moving step includes injecting a quantity of insulin into the patient in response to the determined blood glucose concentration. The method may also include automatically injecting a quantity of insulin into the patient in response to the determined blood glucose concentration. The determining step may include sampling a fluid taken from the patient with a second electrokinetic pump.

In some embodiments the method includes monitoring a parameter (e.g., flow rate, pump element position) related to an amount of dispensed fluid moved out of the third reservoir during the moving step and may include using the monitored parameter to provide feedback control of the moving step. The monitored parameter may be used to provide an indication related to the dispensed fluid, to calculate a desired amount of dispensed fluid to be dispensed, and/or to indicate the presence of an occlusion in the pump outlet.

In some embodiments, the moving step further includes moving dispensed fluid out of the third reservoir for a fixed time interval to dispense a fixed volume of dispensed fluid. The method may also include adjusting an amount of dispensed fluid moved out of the third reservoir.

In some embodiments, the method includes loading the dispensed fluid into the third reservoir and treating the electrokinetic pump to alter a characteristic of the dispensed fluid, such as by irradiating the electrokinetic pump.

In some embodiments the method includes moving pump fluid from the second reservoir to the first reservoir after the first moving step.

In some embodiments, the moving step includes moving substantially all of the pump fluid out of the reservoir substantially without the occurrence of Faradaic processes in the pump. The method may also include moving the pump fluid out of the reservoir at a flow rate of less than about 1 microliter/minute and with a steady state flow rate error of no more than about 5% over the entire method step and/or generating a pump fluid pressure between about 1 and about 1000 psi.

In embodiments wherein the electrokinetic pump further includes a power source connectable to the electrodes and a housing containing the electrodes, dielectric material, reservoir and power source, the electrokinetic pump may have a volume of at most about 11 $cm^3$, the moving step further includes moving at least about 0.2 milliliters of pump fluid. The moving step may include moving the pump fluid at a rate of less than about 10 nanoliters/min and possibly includes moving the pump fluid substantially continuously for about 30 days.

In some embodiments, the method includes supporting the electrokinetic pump on a patient, such as by implanting the electrokinetic pump in a patient. The electrokinetic pump has a shape; the implanting step therefor may include placing the electrokinetic pump adjacent to an anatomical feature of the patient having a shape complementary to the electrokinetic pump shape.

In some embodiments in which the electrokinetic pump includes a first electrokinetic pump, and the moving step includes moving pump fluid at a first rate into a patient, the method further includes: providing a second electrokinetic pump including a pair of double-layer capacitive electrodes connectable to a power source, a porous dielectric material disposed between the electrodes and a reservoir of a pump fluid; connecting the electrodes of the second electrokinetic pump to a power source; and moving pump fluid out of the second electrokinetic pump reservoir at a second rate into the patient substantially without the occurrence of Faradaic processes in the second pump.

In some embodiments, the connecting step may include connecting the power source to the electrodes in a time modulated manner, alternating the power source between an on state and an off state or alternating the power source between a normally off state and a periodic on state in response to a computer program.

Another aspect of the invention provides an electrokinetic pump system which includes: a pair of double-layer capacitive electrodes having a capacitance of at least $10^{-2}$ Farads/$cm^2$; a porous dielectric material disposed between the electrodes; a reservoir containing pump fluid; and a power source connected to the electrodes; the electrodes, dielectric material and power source being adapted to move the pump fluid out of the reservoir substantially without the occurrence of Faradaic processes in the pump. The pump system may further include a pump outlet, the electrodes, dielectric material and power source being further adapted to move the pump fluid out of the reservoir and through the pump outlet.

In some embodiments, wherein the reservoir is a first reservoir, the system further includes a second reservoir, the electrodes, dielectric material and power source being further adapted to move the pump fluid out of the first reservoir and into the second reservoir. The system may further include a third reservoir containing dispensed fluid and a pump outlet, the electrodes, dielectric material and power source being further adapted to move the dispensed fluid out of the pump outlet as the pump fluid moves from the first reservoir into the second reservoir and possibly an indicator adapted to indicate an amount of dispensed fluid present in the third reservoir. The system may also include a controller adapted to control delivery of power from the power source to the electrodes to move a fixed volume of dispensed fluid out of the third reservoir, to control delivery of power from the power source to the electrodes to move dispensed fluid for a fixed period of time, to control delivery of power from the power source to the electrodes to move dispensed fluid out of the third reservoir at a fixed time interval, and/or to control delivery of power from the power source to the electrodes to move an amount dispensed fluid out of the third reservoir in response to a user input.

In some embodiments in which a first electrokinetic pump includes the electrodes, the first, second and third reservoirs, the pump outlet, the dielectric material and the power source, the pump outlet includes a first pump outlet, the first electrokinetic pump being adapted to move dispensed fluid into a patient through the first pump outlet; and the system further includes a second electrokinetic pump includes a second pair of double-layer capacitive electrodes connectable to a power source, a porous dielectric disposed between the second pair of electrodes, a fourth reservoir containing pump fluid, a second reservoir and a sixth reservoir containing a dispensed fluid, and a second pump outlet, the second electrokinetic pump electrodes and dielectric material being adapted to move the second electrokinetic pump fluid out of the fourth reservoir into the fifth reservoir to move the second electrokinetic pump dispensed fluid through the second pump outlet into the patient when the second electrokinetic pump electrodes are connected to a power source substantially without the occurrence of Faradaic processes in the second pump, and the system further includes a controller adapted to control the first and second electrokinetic pumps. The first electrokinetic pump may be further adapted move dispensed fluid at a first rate and the second electrokinetic pump is further adapted to move dispensed fluid at a second rate different than the first rate.

In embodiments in which a first electrokinetic pump includes the electrodes, the first, second and third reservoirs, the pump outlet, the dielectric material and the power source, the first electrokinetic pump being adapted to move dispensed fluid into a patient; the system may further include a second electrokinetic pump with a pair of double-layer capacitive electrodes connectable to a power source, a porous dielectric disposed between the electrodes, a fourth reservoir containing pump fluid, a fifth reservoir and a sixth reservoir containing a dispensed fluid, the second electrokinetic pump electrodes and dielectric material being adapted to move the second electrokinetic pump fluid out of the fourth reservoir into the fifth reservoir to move the second electrokinetic pump dispensed fluid through the pump outlet into the patient when the second electrokinetic pump electrodes are connected to a power source substantially without the occurrence of Faradaic processes in the second pump. The first electrokinetic pump may be further adapted move dispensed fluid at a first rate and the second electrokinetic pump is further adapted to move dispensed fluid at a second rate different than the first rate.

In embodiments in which a first electrokinetic pump includes the electrodes, the first, second and third reservoirs, the pump outlet, the dielectric material and the power source, the first electrokinetic pump being adapted to move dispensed fluid into a patient; the system may further include a second electrokinetic pump with a pair of double-layer capacitive electrodes connectable to a power source, a porous dielectric disposed between the electrodes, a fourth reservoir containing pump fluid and a fifth reservoir, the second electrokinetic pump electrodes and dielectric material being adapted to move the second electrokinetic pump fluid out of the fourth reservoir into the fifth reservoir to move the dispensed fluid through the pump outlet into the patient when the second electrokinetic pump electrodes are connected to a power source substantially without the occurrence of Faradaic processes in the second pump.

In some embodiments, the system further includes a movable member disposed between the second reservoir and the third reservoir adapted to move as pump fluid moves from the first reservoir into the second reservoir to move the dispensed fluid out of the third reservoir. The movable member may include a hydraulic amplifier.

In some embodiments, the system further includes a sensor adapted to determine a patient's need for the dispensed fluid. The system may also have a controller adapted to control delivery of power from the power source to the electrodes in response to a signal from the sensor. The sensor may include an electrokinetic pump adapted to sample a fluid from the patient.

In some embodiments the system further includes a third reservoir containing a sampled fluid and a pump inlet, the electrodes, dielectric material and power source being further adapted to move the sampled fluid into the pump inlet as the pump fluid moves from the first reservoir into the second reservoir. The system may also have a movable member disposed between the second reservoir and the first reservoir adapted to move as pump fluid moves from the first reservoir into the second reservoir to move the sampled fluid into the third reservoir.

In some embodiments the system further includes a third reservoir, an external port communicating with the third reservoir and a movable member disposed between the second reservoir and the third reservoir adapted to change an effective volume of the third reservoir as an effective volume of the second reservoir changes. The system may also include a laminated housing, the electrokinetic pump system having a volume no greater than 250% of the largest effective volume of the third reservoir. The third reservoir may include, e.g., a syringe or a collapsible container. The system may also include a sensor adapted to monitor a parameter related to an amount of fluid dispensed from the third reservoir and possibly a feedback control element adapted to control power delivered to the electrodes by the power source in response to a signal from the sensor. The sensed parameter may be flow rate of fluid dispensed from the third reservoir and/or a position of a syringe. A controller adapted to control application of power from the power source to the electrodes may be provided to respond to a sensor output signal. The system may also include an indicator adapted to provide an indication related to fluid dispensed from the third reservoir, such as the presence of an occlusion of the external port.

In some embodiments, the electrodes, dielectric material and power source are further adapted to move substantially all of the pump fluid out of the reservoir substantially without the occurrence of Faradaic processes in the pump. In some embodiments, the electrodes, dielectric material and power source are further adapted to move substantially all of the pump fluid out of the reservoir at a flow rate of less than about 1 microliter/minute and with a steady state flow rate error of no more than about 5% substantially without the occurrence of Faradaic processes in the pump. In still other embodiments, the electrodes, dielectric material and power source are further adapted to generate a pump fluid pressure between about 1 and about 1000 psi.

Some embodiments further include a housing having a volume of at most about 11 cm³ and wherein the electrodes, dielectric material and power source are further adapted to move at least about 0.2 milliliters of pump fluid from the reservoir. In some embodiments, the electrodes, dielectric material and power source are further adapted to move pump fluid from the reservoir at a rate of less than 10 nanoliters/min. In other embodiments, the electrodes, dielectric material and power source are further adapted to move pump fluid from the reservoir from the reservoir substantially continuously for about 30 days.

In some embodiments, the housing includes a laminated housing. The electrodes, dielectric material and power source may be further adapted to be implanted in a patient or worn on the body. The system may include an indicator adapted to indicate an amount of pump fluid present in the reservoir and may include a controller adapted to provide power from the power source to the electrodes in a time modulated manner, to alternate the power source between an on state and an off state, and/or to alternate the power source between a normally off state and a periodic on state in response to a computer program.

Another aspect of the invention provides a displacement pump including: a dispensed fluid reservoir; a pump outlet; a displacement mechanism; a power source adapted to operate the displacement mechanism; and a housing containing the reservoir, pump outlet, power source and displacement mechanism, the housing having a volume no more than 250% of the volume of the dispensed fluid reservoir; the displacement mechanism and power source being further adapted to dispense substantially all of dispensed fluid from the reservoir through the pump outlet at a flow rate no more than 1 microliter/minute with a steady state flow rate error of no more than about 5%. The displacement mechanism may include a movable member. The displacement mechanism may also include an electrokinetic assembly including a pair of electrodes connectable to the power source, a porous dielectric material disposed between the electrodes; and pump fluid in contact with the electrodes, and the electrodes may be double-layer capacitive electrodes.

Yet another aspect of the invention provide a reservoir of pump fluid; a pump mechanism operable on the pump fluid; a pump outlet; a power source connectable to the pump mechanism to move pump fluid from the reservoir through the pump outlet at a flow rate no more than 1 microliter/minute with a steady state flow rate error of no more than about 5%; and a housing containing the reservoir, electrodes, pump outlet and power source, the housing having a volume no more than 150% of the volume of the reservoir. In some embodiments, the pump mechanism includes a pair of double-layer capacitive electrodes having a capacitance of at least $10^{-2}$ Farads/cm².

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates a cross-sectional view of one embodiment of a direct EK pump;

FIG. 2 illustrates a cross-sectional view of a direct EK pump comprising a split reservoir design;

FIG. 3 illustrates a cross-sectional view of an indirect EK pump;

FIG. 9 illustrates the dependence of fluid flow rates on voltage of an EK pump;

FIG. 10 illustrates the relationship of pressure and fluid flow rate of an EK pump;

FIG. 11a illustrates one embodiment of a flow indicator;

FIG. 11b illustrates one embodiment of a flow meter;

FIG. 12b illustrates a schematic view of the EK delivery system illustrated in FIG. 12a;

FIG. 13b illustrates a schematic view of the EK delivery system illustrated in FIG. 13a;

FIGS. 20-23 illustrate pump performance wherein:

FIG. 20 graphically illustrates rapid loading and delivery flow rates of an EK pump;

FIG. 21 graphically illustrates the constant steady-state flow rates during operation of an EK pump at any instantaneous time; and FIGS. 22 and 23 graphically illustrate constant steady-state flow rates during operation of an EK pump configured to operate over a period of hours or days.

DETAILED DESCRIPTION OF THE INVENTION

Figure 4A:
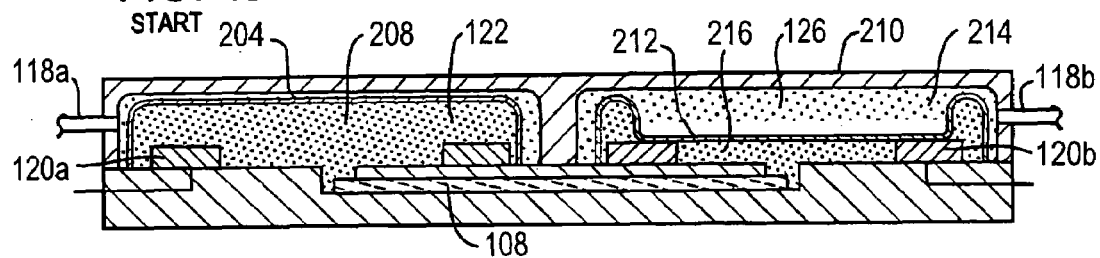
FIGS. 4a-4c schematically illustrate operation of the EK pump provided in FIG. 3.

The invention described herein provides EK systems for efficient, reliable and precise movement of a pump fluid for drug delivery and/or analyte sampling. Before describing these systems, the designs and characteristics of a few exemplary EK pumps suitable for use in said systems are provided below.

FIG. 1 is a cross-sectional view of a small, compact EK pump 100. In this example, EK pump 100 comprises a first fluid reservoir 102 and a second fluid reservoir 104. First fluid reservoir 102 is coupled to second fluid reservoir 104 by through-vias 106, 110 and porous dielectric material 108. Through-vias 106 and 110, along with porous dielectric material 108, provide a fluidic path between first reservoir 102 and second reservoir 104. In this example, porous dielectric material 108 is encapsulated within a bonding material 114, between upper and lower substrates 116a and 116b, respectively, as further described in Ser. No. 10/198,223.

Each fluid reservoir further comprises a fluid port 118 (which can be an inlet or outlet port) and capacitive electrode 120a and 120b. An electrical lead (not shown) is placed in contact with electrodes 120a, 120b to couple them to a power supply (not shown). During operation, reservoirs 102 and 104, including the space between porous dielectric material 108 and electrodes 120a and 120b, is filled with an electrolyte or pump fluid 122. The fluid 122 may flow though or around electrodes 120a and 120b. As a voltage (correlated to the desired flow rate and pressure profile of pump 100) is applied, pump fluid 122 is moved from one fluid reservoir to the other via electro-osmosis, without electrolysis, gas generation or substantial capacitive de-ionization during operation of the pump 100. As will be recognized by one skilled in the art, gas formation or pH change due to changes in pump components (e.g., the pump fluid and/or electrodes), can introduce system error and decrease the precision of a fluid transport system or prevent the pump from working altogether.

Generally, the problem of gas formation and pH change in prior EK pumps results from electrochemical changes in the pump components, which are induced when a high enough electric field or voltage is applied to create a desired EK flow. For example, the pump fluid may be oxidized or reduced and produce gas and/or change the pH. Additionally, the electrodes of prior art EK pumps can be changed by oxidation-reduction reactions at the electrode-pump fluid interface. As will be recognized by one skilled in the art, these Faradaic processes decrease the precision and operability of EK pumps over time. To prevent or minimize Faradaic processes, several techniques can be employed in this invention, including but not limited to, implementing drive strategies to limit Faradaic processes and careful material selection of pump electrodes.

For example, a system voltage and the duration of the applied system voltage should be maintained sufficient to charge the electrodes and generate current flow to support a desired fluid flow rate for a given length of time, but below an electrode charging potential beyond which Faradaic reactions (such as oxidation/reduction) are induced. However, current flow is required in order to provide pump fluid flow. What is needed is a non-Faradaic process for maintaining current flow and fluid flow. This challenge can be met by employing electrodes having high double layer capacitance. Use of high double layer capacitance electrodes ensures that an applied system voltage will be sufficiently high to charge the electrodes and support the desired current and fluid flow of most pump fluids (such as water, saline, etc.) but be below an electrode charging potential beyond which oxidation-reduction is induced. Accordingly, configuration of an EK pump to move a pump fluid without the occurrence of Faradaic processes includes the incorporation of electrodes made of materials having a high double-layer capacitance of at least $10^{-4}$ Farads/cm$^2$, more preferably of at least $10^{-2}$ Farads/cm$^2$, and most preferably of at least 1 F/cm$^2$. Preferably, these high double-layer capacitance electrodes are compatible with a wide range of pump fluids.

In general, high capacitance of double-layer materials arises from their comparatively large microscopic surface area. In one example, carbon paper impregnated with a carbon aerogel can be used as a high capacitance double-layer electrode. Other forms of carbon also have very large microscopic surface areas and exhibit double-layer high capacitances, and thus may be employed herein. For example, shaped carbon aerogel foam, carbon mesh, carbon fiber (e.g., pyrolized poly(acrylonitrile) or cellulose fiber), carbon black and carbon nanotubes, all of which have significant double layer capacitances.

While double-layer capacitive electrodes may also be formed of materials other than carbon, carbon is the preferred electrode material, as it is also inert and inhibits or slows reactions detrimental to EK transport of a fluid, i.e., Faradaic reactions (such as oxidation reduction of the electrodes or pump fluid). Further, the use of carbon based electrodes (for example, carbon paper) provides flexibility in EK pump design and configuration, as these materials are shapeable and conformable into a variety of shapes (e.g., can be punched, cast or cut easily into a variety of shapes) and are inexpensive, thus lowering the production costs of the EK pumps provided herein.

With respect to drive strategies to minimize Faradaic processes, a pump can be operated at system voltages, and the system voltages applied for durations, below a potential, or threshold, beyond which Faradaic processes such as electrolysis of the pump fluid is induced. Pump fluid electrolysis potentials for most pump fluids are less than a few volts; for example, the electrolysis potential for water is about 1.2 V while the electrolysis potential for propylene carbonate pump fluid is about 3.4 V. By maintaining a voltage drop across the electrodes of a pump below this electrolysis potential, pump fluid electrolysis can be prevented or minimized. The use of double layer high capacitance electrodes allows high or low system voltages to be used to support EK fluid flow through the pump without causing Faradaic processes in the pump fluid or electrodes. If the threshold for electrode oxidation or reduction is lower than that of the pump fluid, driving strategies can be employed that apply a system voltage and the duration of the applied system voltage sufficient to charge the electrodes and generate current flow to support a desired fluid flow rate for a given length of time, but below an electrode charging potential beyond which Faradaic reactions (such as oxidation/reduction) of the electrodes are induced.

In addition, to prevent capacitive deionization of a pump fluid (which is a non-Faradaic process but can still impact pump performance), it may also be preferable to employ a pump fluid having a sufficiently high enough ionic strength, so that during operation, the pump fluid's ionic strength does not fall below a minimum pump fluid ionic strength needed to support electro-osmotic flow since deionization of a pump fluid occurs over time, reducing the conductivity of the pump fluid. Yet another approach can be to limit the volume of pump fluid (or other fluid) in a pump reservoir that can be transported during a given run time of a pump before complete deionization of the pump fluid occurs.

In yet another embodiment, the pump design itself can be adapted to minimize the effect of deionization processes that can decrease the operability of a pump over time. For example, in the embodiment illustrated in FIG. 2, the shape of the first fluid reservoir 102 may be tapered in the portion of said reservoir immediately surrounding an electrode, creating a low volume fluidic path over the electrode. As will be recognized by those skilled in art, this low volume reservoir 124 configuration creates a steady state ion concentration adjacent to the electrode 120a, as the rate of ions passing into a low volume reservoir 124 is generally proportional to the rate of deionization of the pump fluid 122 which usually occurs during operation of a pump. In this way, the effects of deionization of the pump fluid 122 on pump flow rate and current can be minimized and controlled during pump operation.

FIG. 3 illustrates yet another embodiment of an EK pump 200 in accordance with the present invention. In this example, pump 200 is configured as an indirect pump. As provided herein, an indirect pump is a pump where movement of a pump fluid 122 causes flow of a second fluid in a separate part of the pump. This second fluid is referred to herein as a working fluid 126, which may be a drug or other fluid to be dispensed by pump 200.

In this embodiment, EK pump 200 generally comprises a first chamber 202 comprising: a first flexible barrier 204 separating first reservoir 206 and second reservoir 208; and a second chamber 210 comprising a second flexible barrier 212 that separates third reservoir 214 and fourth reservoir 216. Either of ports 118 may be an outlet for the working fluid, an inlet for the working fluid and/or a vent for one of the working fluid reservoirs. Preferably, flexible barriers 204 and 212 are impermeable to prevent mixing of a pump fluid 122 (disposed in second 208 and fourth 216 reservoirs) and working fluid 126. This pump configuration may be used when a working fluid (e.g., drug, reagent, etc.) is not compatible with electrokinetic flow; when the working fluid does not support a zeta potential, has a low electrolysis potential, has a high viscosity, or has or carries suspended particles or cells; or in cases where long-term storage, or useable lifetime, of the working fluid requires that it be separate from the pump fluid. In pump 200, a fluidic pathway exists between second 208 and fourth 216 fluid reservoirs by means of porous dielectric material 108, which may be encapsulated within a bonding material disposed between upper and lower substrates (as in FIG. 1) or disposed within a conduit, or plurality of conduits. Electrodes 120a and 120b surround openings leading to and from porous dielectric material 108.

Figure 4B:
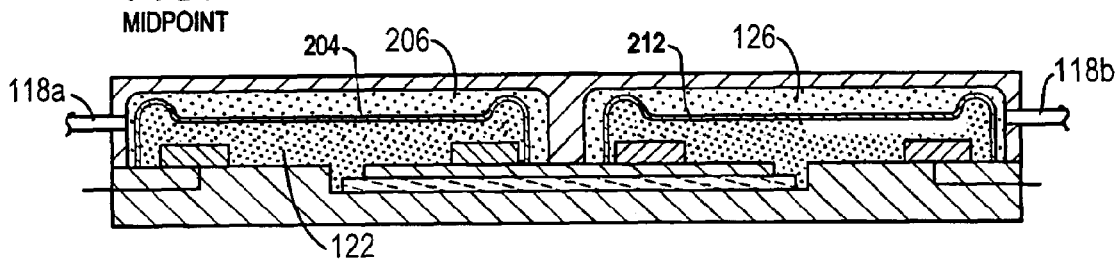
Figure 4C:
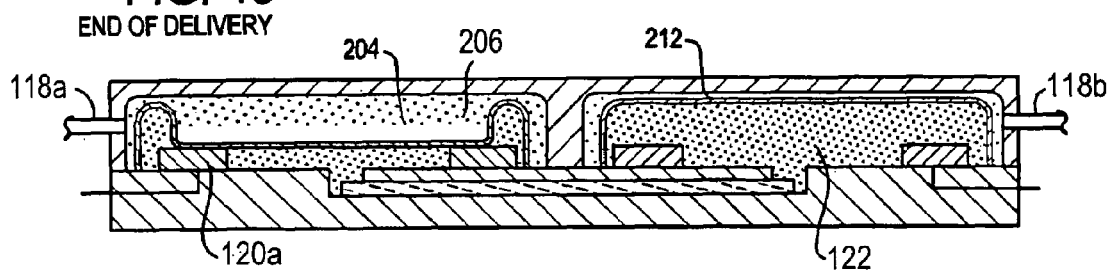

FIGS. 4a-4c are provided to illustrate what happens during operation of pump 200 as a voltage is applied across electrodes 120a and 120b disposed within second 208 and fourth 216 reservoirs respectively. In general, as pump fluid 122 is pumped from second reservoir 208, through porous dielectric material 108, and into fourth reservoir 216, first flexible member 204 is collapsed while second flexible member 212 disposed with the second chamber 210 is distended. As the second flexible member 212 is distended working fluid 126 (which may be a drug, etc) disposed within the third reservoir 214 will be displaced and pumped out of third reservoir 214 through a fluid port 118b. The volume in first reservoir 206 may be filled through port 118a with additional working fluid, air, etc., as flexible member 204 moves to expand first reservoir 206 and contract second reservoir 208.

Figure 5A:
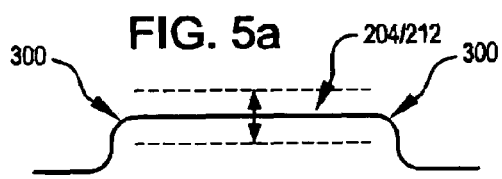
FIGS. 5a-5c schematically illustrate controlled collapse of impermeable membranes during operation of the EK pump illustrated in FIGS. 3 and 4.
Figure 5B:
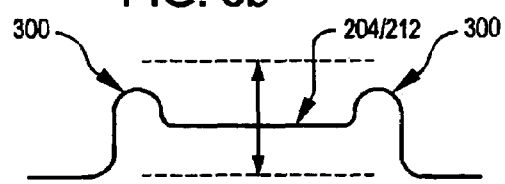
Figure 5C:
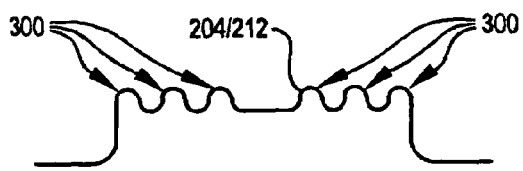

In pump configurations where flexible members 204, 212 are employed, it may be advantageous to utilize flexible members having highly ordered movement during collapse or expansion as depicted in FIGS. 5a-5c. As illustrated in FIGS. 5a-c, a pump may be configured to comprise a flexible member that has a single flexure joint 300 (indicated by arrows) giving rise to a simple geometry during collapse (or expansions), as shown in FIG. 5a, or multiple or compound geometries during collapse, as pictured in FIGS. 5b and 5c. As will be appreciated by those skilled in the art, this feature will ensure precise and maximal fluid movement effected by the pump, especially if the pump is adapted for small volume movement of liquids, low flow rates or low pressures.

In general, the pumps provided herein (including both direct and indirect pump embodiments) are highly compact and not much larger than the volume of a fluid to be transported by the pump. Accordingly, in the present invention the various systems incorporating these pumps for fluid transport can be correspondingly small. For example, for a drug delivery pump system (i.e., the electrodes, dielectric conduit, and reservoirs without the power supply or control electronics), the volume of said system need not be greater than about 250% of the largest effective volume of a drug reservoir if an indirect pump configuration is employed. For a pump system comprising a direct pump configuration such as the one shown in FIGS. 1 and 2, the volume of a pump system need no be more than 150% of the largest effective volume of a drug reservoir.

Figure 6:
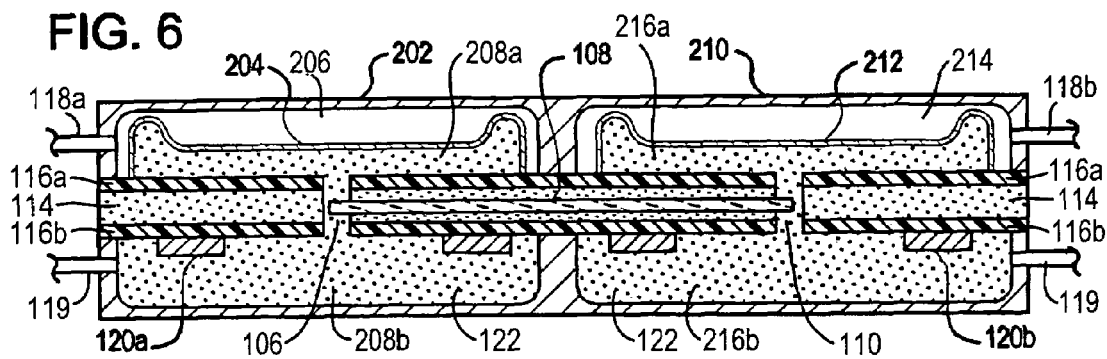
FIG. 6 illustrates a cross-sectional view of another indirect EK pump embodiment.

FIG. 6 illustrates another technique that can be employed to ensure maximal and precise fluid delivery from an EK pump. Through-vias 106 and 110 extend through a laminated substrate 116a and 116b to form upper and lower parts 208a, 208b, 216a, 216b of the pump fluid reservoirs. In this example, the flexible members 204 and 212 define the upper reservoir parts 208a and 216a while the electrodes 120a and 120b of pump 300 are placed within lower reservoir parts 208b and 216b so that flexible members 204 and 212 are not in contact with the electrodes 120a and 120b during collapse. As will be appreciated by one skilled in the art, this placement of electrodes inside of reservoirs 208 and 214 increases the fluid volume/capacity of the pump. Filling ports 119 are used to fill the reservoirs 208a and 208b and reservoirs 216a and 216b with pump fluid 122 during pump manufacture and are sealed during pump operation.

Figure 7:
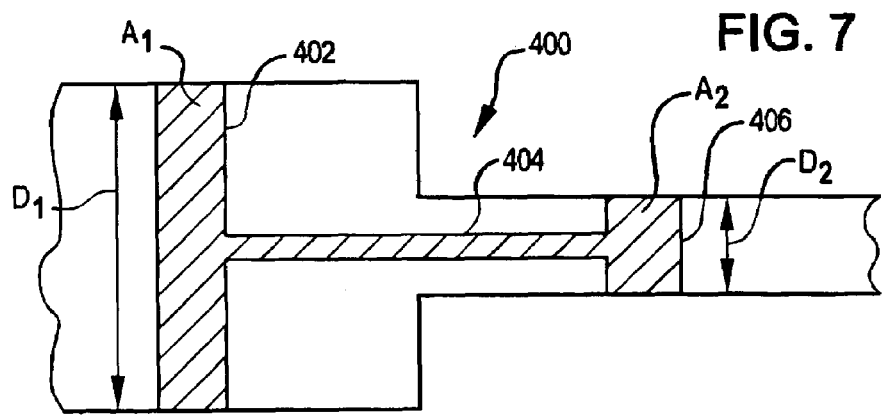
FIG. 7 illustrates a cross-sectional view of one embodiment of a hydraulic amplifier.

FIG. 7 illustrates another feature that may be incorporated to modulate fluid flow rates from an EK pump, a hydraulic amplifier 400. In one embodiment, hydraulic amplifier 400 comprises a first piston 402 having a first cross-sectional area A1 and diameter D1 and a rigid shaft 404 that couples first piston 402 to second piston 406 having a second cross-sectional area A2 and diameter D2.

During operation, fluid (e.g., a pump fluid) from a pump may be directed against the first piston 402, which displaces the first piston 402 and the second piston 406 in a first direction. Alternatively, fluid may be directed against the second piston 406 to displace it and the first piston 402 in the opposite direction. As will be recognized by those skilled in the art, hydraulic amplifier 400 may be used to create pressure amplification or de-amplification as well as flow reduction or increase as may be needed. Accordingly, by appropriately choosing the relative piston sizes, the pressure and flow characteristics of a pump may be modulated.

In the embodiment shown in FIG. 7, linear displacement of the pistons 402 and 406 is generally equal. However, because of the differing cross-sectional areas of the respective pistons provided by the differences in diameters of the pistons, pressure amplification (or de-amplification) proportional to the ratio of the cross-sectional areas is created. In one example, the use of hydraulic amplifier can be used to alter the flow rate of a dispensed fluid vs. the flow rate of a pump fluid; for example a hydraulic amplifier can be used so that a dispensed fluid flow rate of a drug is between about 0.1 times and 10 times a pump fluid flow rate.

Figure 8:
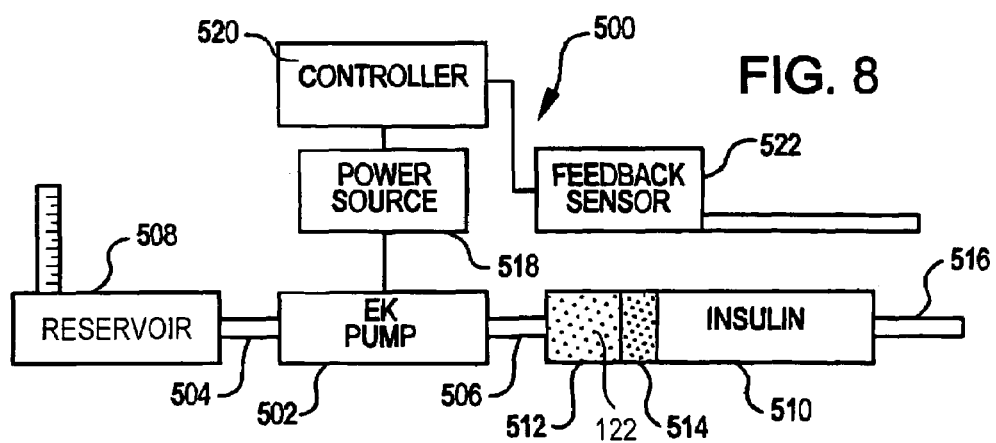
FIG. 8 illustrates one embodiment of an EK delivery system comprising a syringe.

Further detailed descriptions of various compact, precise and low-cost medical systems for drug delivery and/or analyte systems are provided below. As further described herein, these EK systems are smaller, lighter and more cost-effective than comparable prior systems and offer advantages in design flexibility and simplicity due to the incorporation of EK pumps for general fluid transport to effect drug delivery, analyte sampling, etc., FIG. 8 is a schematic diagram of one embodiment of an EK delivery system 500 in accordance with the present invention. EK delivery system 500 preferably comprises EK pump 502 having an inlet 504 and outlet 506 fluid port; a reservoir 508; a syringe 510 having a pump fluid chamber 512, plunger 514, a syringe port 516; a power source 518; and a system controller 520 having one ore more feedback sensors 522. In this embodiment, inlet fluid port 504 is coupled to reservoir 508 and outlet fluid port 506 is coupled to a syringe 510, containing, for example, a drug such as insulin, pain medication or other therapeutic or diagnostically useful agent.

In one embodiment of system 500, pump 502 is configured to move a drug out of syringe 510 and into a patient. Reservoir 508 can contain a pump fluid 122 while syringe 510 may be loaded with a drug. During operation, EK pump 502 (via direction of controller 520) causes movement of the pump fluid 122 into pump fluid chamber 512 of syringe 510 and creates hydraulic pressure that pushes against syringe plunger 514, causing movement of the plunger 514 and effecting drug delivery.

As will be recognized by those skilled in the art, syringe 510 can be configured to couple to any patient access device, such as a conventional infusion set, port-a-catheter, IV needle and the like, for transdermal, transvascular, intramuscular delivery of a drug into a patient. Alternatively, system 500 can be configured as a small ambulatory system contained in a bio-compatible, preferably inert housing, which is hermetically sealed to prevent leakage of any system components. As will be appreciated by one skilled in the art, because the EK systems of the present invention do not require mechanical components to cause fluid transport and drug delivery, these devices are small and lightweight and can be configured in any shape so that they can be easily carried or worn by a patient and hidden from view. Moreover, syringe 510 and reservoir 508 can be adapted to be refillable. In yet another embodiment, system 500 can be coupled to a transcutaneous adhesive pad having a plurality of micro-needles to adapt system 500 as a transdermal delivery system.

As will be further appreciated by those skilled in the art, system controller 520 serves to control the operation of pump 502 (e.g., to effect fluid flow rates, pressures, etc.), preferably in response to one or more system feedback sensors 522. These feedback sensors 522 can be installed in any location, and their signals can be transmitted through a sensing circuitry, which can be integrated into system controller 520. Various signals from these feedback sensors 522 can be configured to provide feedback regarding drug volume displacement; measurements of flow rate or delivery rate over time; battery life; drug and pump reservoir conditions; system component malfunctions; the presence of an occlusion or other flow obstruction or failure; and other data. Preferably, the feedback data is transmitted quickly so that dynamic responses by the system controller 520 in response to feedback data can be initiated.

In one specific embodiment, a feedback sensor 522 can be coupled to syringe plunger 514 to detect and monitor displacement of plunger 514. In one exemplary embodiment, feedback sensor 522 may be a magnetostrictive sensor available from MTS Sensors, of Cary, N.C., and the plunger 514 may contain an embedded permanent magnet. As will be recognized by one skilled in the art, these sensors can provide absolute distance measurements of plunger 514 without needing to be zeroed to an external reference. By monitoring the distance moved by plunger 514 at a given time, the amount of a substance delivered by system 500 can be compared to the desired amount of a substance to be delivered and the operation of the pump modulated at selected time intervals to ensure precise accurate delivery. Pump modulation may involve modifying drive voltage, current or duration of pump operation. Preferably, data from feedback sensor 522 is relayed to controller 520 where displacement of the plunger 514 can be correlated to the amount of agent/drug delivered by system 500. Depending on the desired drug dosage regime, the controller 520 can modulate operation of pump 502 (by regulating current and voltage applied to the pump) to achieve the appropriate drug delivery profile. In one embodiment, depending on whether less or more drug delivery is required, operational parameters of the pump may be modulated.

For example, flow rates can increase or decrease based on feedback from sensors 522 disposed on plunger 514 by altering the voltage applied to the electrodes disposed in pump 502. FIG. 9 graphically illustrates this concept and depicts the direct relationship of an EK pump voltage with the pump flow rate. FIG. 10 is provided to illustrate the relationship between pressure and flow rate. FIGS. 9 and 10 also depict performance aspects of the EK and demonstrate the precision and consistent flow rates and pressures during'steady state fluid flow using the EK pumps of the present invention. Alternatively, controller 520 can simply apply power to the electrodes according to a preset on and off cycle (e.g., where the power is normally off and is turned on to dispense fluid from the syringe) according to a computer program, timer or other control. Use of a timing circuit or other timing control to turn the power on for a period of time can be used to deliver a fixed volume or bolus from the syringe. The system controller can also be provided with a user interface so that a user can indicate or change the volume or size of the bolus delivered.

In yet another embodiment, as illustrated in FIGS. 11a and 11b, flow indicators 600 and flow meters 602 may be disposed in, or coupled to, one or more fluid paths of an EK system, to provide indication of the amount (volume) of a drug dispensed, the amount of agent still remaining in a syringe, the amount of fluid pump fluid remaining in a system reservoir, flow rate, etc., In some examples, said flow indicators 600 and flow meters 602 can provide a visual indication to a system user, or can be functionally coupled to a controller and adapted to supply electronic signals indicative of such information to enable modulation of a EK pump, as needed. In yet another embodiment, pump chamber 512 can be adapted as a hydraulic amplifier to alter the flow rate of a drug from syringe 510 and/or the flow rate of the pump fluid into pump chamber 512.

Figure 12A:
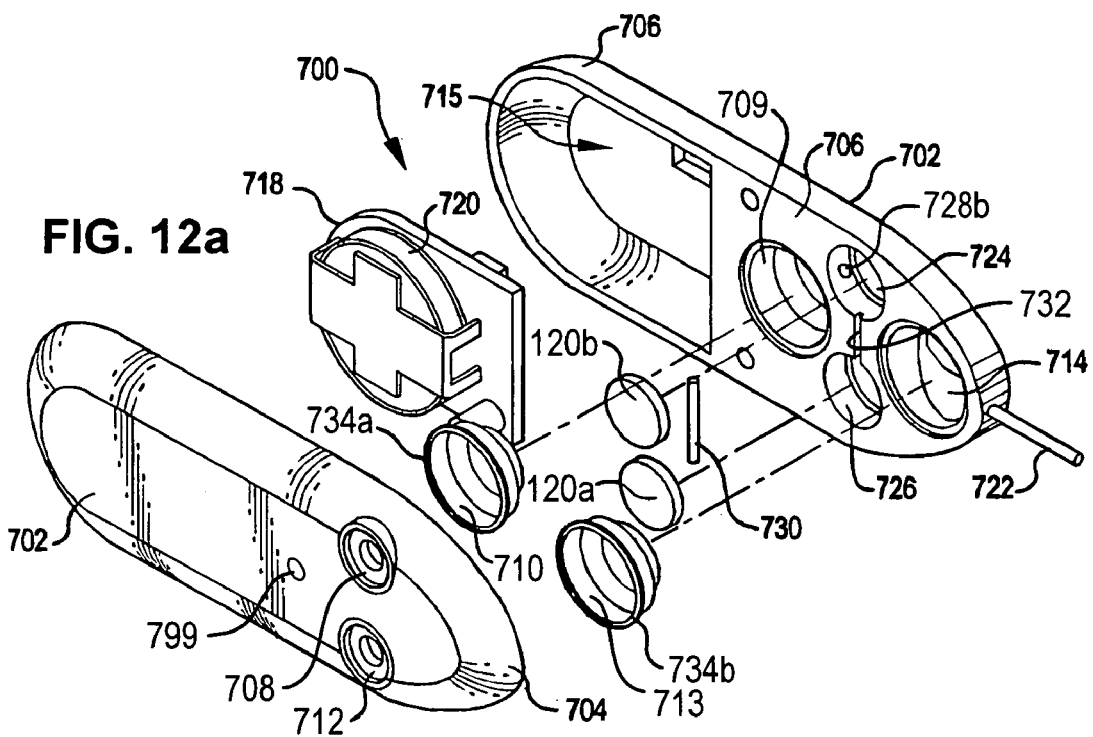
FIG. 12a illustrates an exploded, enlarged view of one embodiment of an EK delivery system.
Figure 12B:
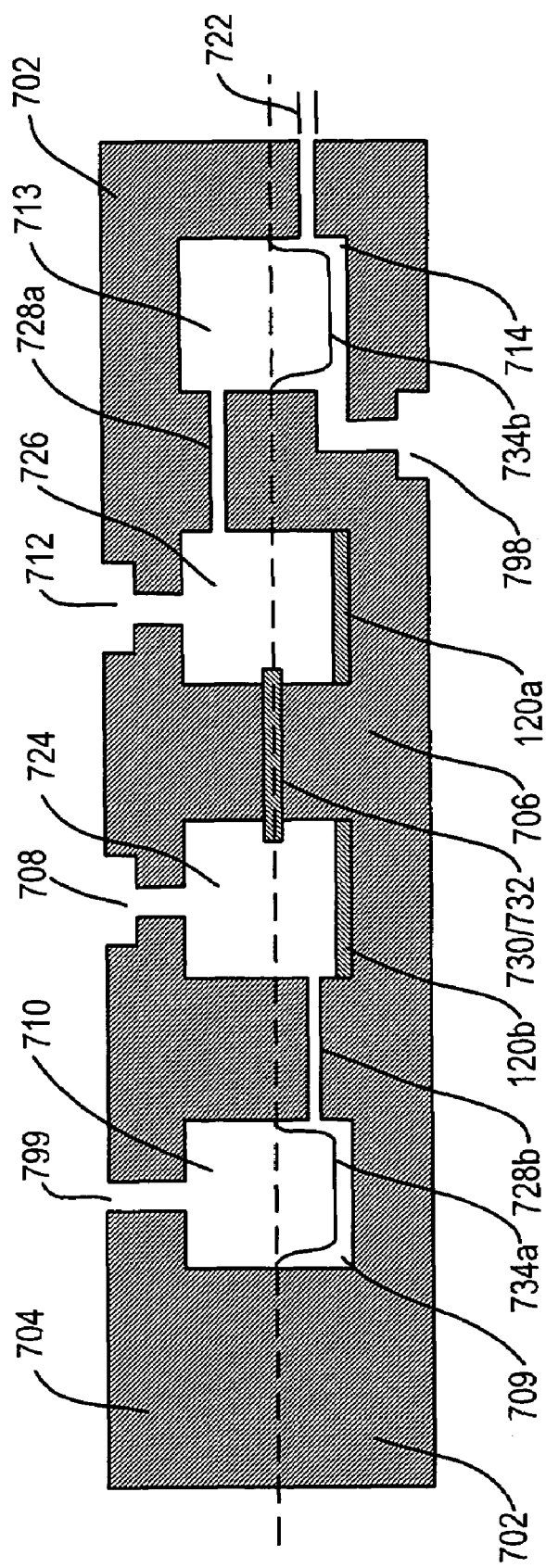

In yet another embodiment, feedback mechanisms can be employed in order to create a feedback loop directly to the EK pump to control activation of a voltage from a battery or power source to the electrodes. For example, a small processor can be designed to produce an activation signal for a selected signal duration, e.g., 1-4 seconds, at selected time intervals to run the EK pump directly, FIGS. 12a-12b illustrate an exploded, enlarged view and a schematic view, respectively, of a self-contained indirect EK pump delivery system 700 in accordance with the present invention. In this example, delivery system 700 is enclosed within housing 702, which includes a first cover 704 and a second cover 706, which can be adhesively bonded together. First cover 704 comprises a first pump fluid aperture 708 and a second pump fluid aperture 712. Apertures 708 and 712 each have a silicone septum which may be pierced by a needle for adding pump fluid to the system. After filling the system with pump fluid, apertures 708 and 712 may be sealed, such as by covering with epoxy.

Second cover 706 houses the internal circuitry of the system in the cavity 715, including a system controller disposed on circuit board 718 and a power source 720. Second cover 706 also houses a first pump fluid reservoir 709 communicating with a second pump fluid reservoir 724 through a through-via 728b, a third pump fluid reservoir 726 communicating with a fourth pump fluid reservoir 713 via a through-via 728*a* (located in the first cover 704—not shown in FIG. 12*a*). Apertures 708 and 712 communicate with reservoirs 724 and 726, respectively. Porous double layer capacitive electrodes 120*a* and 120*b* are disposed in reservoirs 726 and 724, respectively, and the pump fluid in those reservoirs can be moved between reservoirs 726 and 724 (and through reservoirs 709 and 713) through a porous dielectric material 730 (such as packed bed of silica beads) disposed in channel 732 extending between reservoirs 726 and 724 by applying a voltage to electrodes 120*a* and 120*b* from the power source via electrical connections (not shown).

Flexible impermeable diaphragms 734*a* and 734*b* are disposed in second cover 706 to form fifth and sixth reservoirs 710 and 714 adjacent the first and fourth reservoirs 709 and 713, respectively. A vent 799 communicates fifth reservoir 710 with the exterior of the pump, and a cannula 722 serves as an outlet from sixth reservoir 714. In addition, fluid aperture 798 with a silicone septum on the underside of cover 706 provides a way to fill the sixth reservoir 714 with a drug or other fluid to be delivered.

In operation, after filling reservoirs 709, 713, 724 and 726 with pump fluid via, e.g., ports 708 and 712, and sixth reservoir 714 via aperture 798 with a drug, power may be supplied to electrodes 120*a* and 120*b* to move pump fluid from reservoirs 709 and 724 into reservoirs 726 and 713, thereby moving flexible diaphragm 734*b* to dispense the drug from reservoir 714 through cannula 722.

In accordance with this embodiment of the invention, the system 700 is small, having an overall dimension of about 2×0.8×0.4 inches and is configured to deliver about 300 microliters of a drug employing about 300 microliters of a pump fluid. As exemplified in this embodiment, generally the overall size or volume of system 700, (i.e., the volume of the pump less the volume of the power source and circuit board) need not be much greater than the volume of drug to be delivered or the volume of the drug reservoir 714.

Figure 13A:
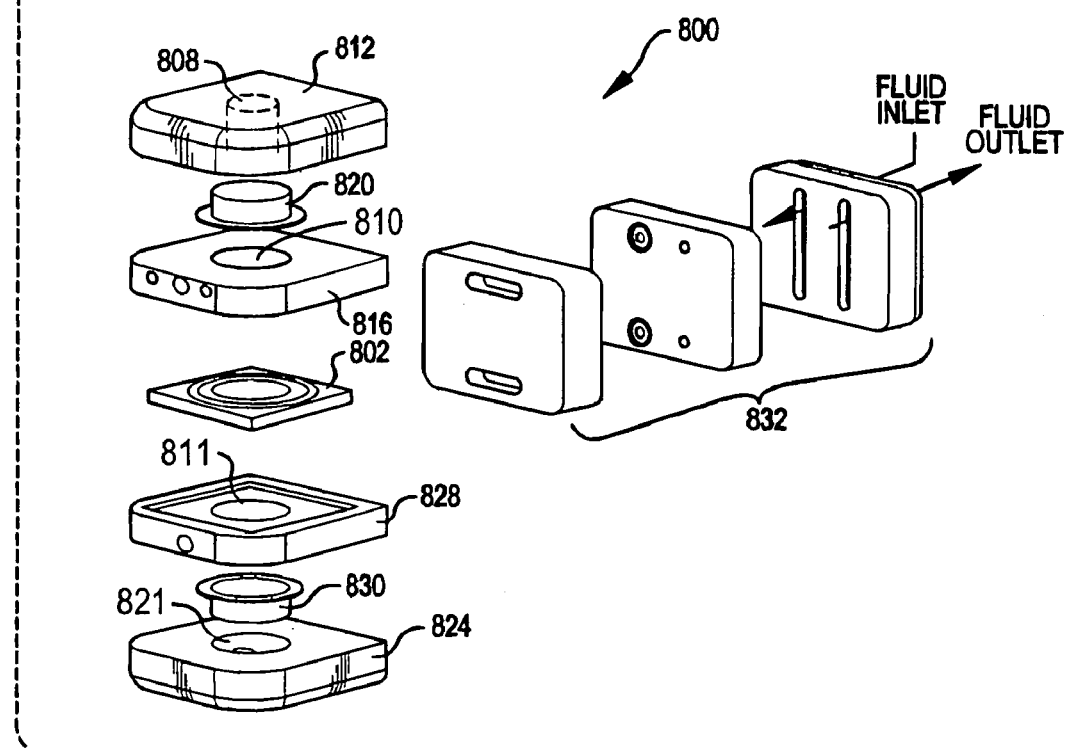
FIG. 13a illustrates an exploded, view of another EK delivery system embodiment.
Figure 13B:
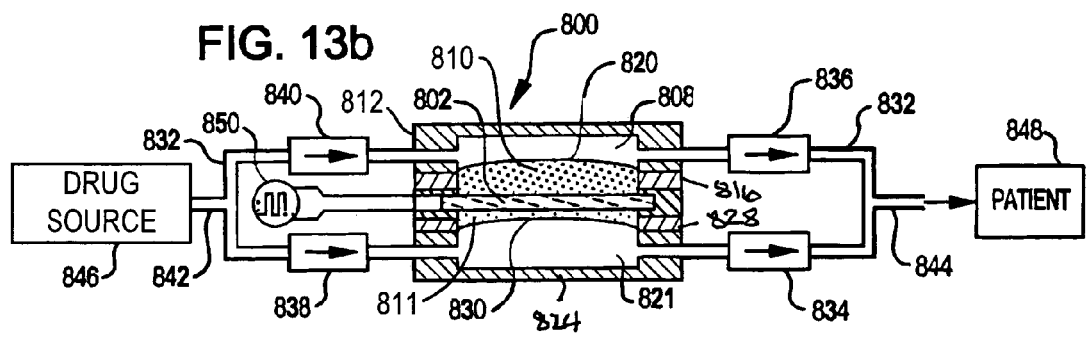

FIGS. 13*a* and 13*b* illustrate yet another embodiment of an EK pump delivery system 800 in accordance with the present invention. In this embodiment, the system is adapted for high flow-rate (about 1-10 mL/min) transport of fluid and which generally comprising electrodes having a porous dielectric material disposed, preferably laminated, between the electrodes so that pump fluid movement is through or perpendicular to the face of the pump as best illustrated in FIG. 13*b*.

FIG. 13*a* illustrates exploded view of one embodiment of EK pump system 800. A flexible diaphragm 820 held between a top housing 812 and a spacer 816 defines a first fluid reservoir 808 and a second fluid reservoir 810. A second flexible diaphragm 830 held between a bottom housing 824 and spacer 828 defines a third fluid reservoir 811 and a fourth fluid reservoir 821. A porous dielectric material 802 separates the second and third reservoirs, which contain EK pump fluid.

Fluid reservoirs 808 and 821 each have fluid inlet and a fluid outlet ports, which couple reservoirs 808 and 821 to fluid pathway 832 (best illustrated in FIG. 13*b*) comprising a plurality of check valves 834, 836, 838 and 840.

As best shown in FIG. 13*b*, system 800 is configured to provide high flow rate unidirectional transport along fluid pathway 832, e.g., movement of fluid from a drug source 846 (such as, e.g., a collapsible IV bag) to system inlet port 842 to system outlet port 844 (which may be coupled to a patient access member 848, such as a needle, infusion set, etc.) and to a patient. As will be appreciated by one skilled in the art, unidirectional fluid transport through system 800 is aided by the one-way check valves 834, 836, 838 and 840 coupled to fluid pathway 832.

In this configuration, voltage from power source 850 is applied to electrodes (not shown) disposed in reservoirs 810 and 811 to cause movement of pump fluid (as indicated by shading) disposed between flexible diaphragms 820 and 830, i.e., from fluid reservoir 810 to fluid reservoir 811, and the direction of flow may be reversed by reversing the polarity of the applied voltage. Movement of the pump fluid from reservoir 810 to reservoir 811 will cause flexible member 820 to move downward, which in turn will draw fluid from drug source 846 to system inlet port 842 and through fluid pathway 832 into reservoir 808. Check valve 836 prevents fluid from being drawn into reservoir 808 from outlet 844. Likewise, fluid in reservoir 821 will be expelled as flexible member 830 moves downward, and check valve 838 prevents the expelled fluid from flowing toward drug source 846. The operation is then reversed by reversing the polarity of the applied voltage, so that pump fluid flows from reservoir 811 into reservoir 810 and diaphragms 820 and 830 move upward. This movement draws the drug into reservoir 821 via check valve 838 and expels drug from reservoir 808 via check valve 836. Check valves 840 and 834 prevent the fluid from flowing in an undesired direction.

The operation of this pump system can be controlled by a controller coupled to the pump, which modulates operation of the pump (by regulating current and voltage, for example amplitude and period or duration, applied to the pump, electrodes, etc.). As will be appreciated by one skilled in the art, the voltage and current applied to the pump and electrodes can be accomplished employing simple or complex drive strategies so that the appropriate pressure, fluid flow rates, drug delivery regimes of the system can be accomplished. Continuous oscillation provides for continuous flow of drug from the drug source to the outlet.

In one exemplary embodiment, system 800 is a small (about 1.6×1.2×1.7 inches) ambulatory system configured to deliver fluids at flow rates of about 1 mL/min at about 1-2 psi. System 800 can be used in place of conventional infusion pump, for example PCA pumps and the like, which are typically coupled to 1 L saline bags. Also, the high accuracy of a low flow rate EK pump can be used to deliver a concentrated version of a drug to a saline stream provided by a higher flow rate pump to provide accurate dosing. EK system 800 can be used similarly and configured for continuous fluid delivery or operation or for intermittent fluid delivery (e.g., by intermittent activation of a system voltage from a battery coupled to turn the system 800 on and off). EK system 800 may also be controlled by feedback (e.g. vary voltage and or current based on a flow sensor reading).

Figure 14:
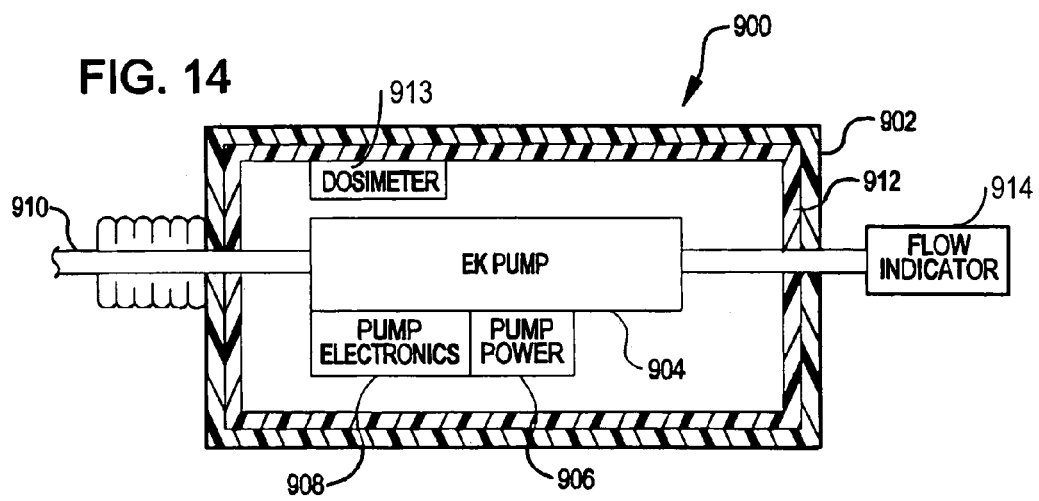
FIG. 14 illustrates a schematic view of one embodiment of a shielded delivery system.

FIG. 14 illustrates yet another embodiment of drug delivery system 900, wherein delivery system 900 is adapted for the delivery of radioactive drugs or other toxic diagnostic or therapeutic compounds that require special handling to minimize a patient or user's exposure to those compound(s). In this example, delivery system 900 comprises a protective or shielded housing 902, which surrounds an EK pump 904; a power source 906; and controller 908. Delivery system 900 further comprises a patient access means 910, which can be a cannula or needle adapted to provide subcutaneous, transvascular or other access to a patient, dosimeter 913, which can be disposed and coupled to a fluid path, reservoir or the like of EK pump 904 to provide indication to a patient/or user regarding a substances delivered, etc., Preferably, the patient access means 910 is shielded to protect the patient or user from the radioactive or toxic material while it is being pumped into a patient.

Delivery system 900 further comprises an internal liner 912, preferably a removable liner, adapted to shield the patient or user from the radioactive or toxic compound contained within the system. To further minimize the need to handle the system during operation, system 900 can further comprise other system components, such as a flow indicator or meter 914; dosimeter 913 (as mentioned above); or other indicator to signal the amount of the toxic substance that has been delivered, how much is left, etc., in order to obviate or minimize the need to handle the system 900 during operation. In one example, indicator 914 can be adapted to be easily viewable by a user or can optionally be omitted and instead an electronic flow meter employed. Moreover, pump 904 and system 900 can be configured to be remotely activated and/or programmable in response to user or automatic control by a pre-programmed controller with feedback control provided by a dosimeter 912, flow indicator dosimeter 914 or the like.

In yet another embodiment, system 900 can be adapted to withstand irradiation to activate a non-radioactive drug preloaded into system 900. Upon irradiation of a preloaded drug within system 900, it is converted into a radioactive form. Therefore, radioactive materials do not need to be handled in order to load a radioactive drug or substance into delivery system 900. Moreover, because of the low cost of the delivery system and EK pump, the entire system 900 can be discarded after use. Yet another advantages to system 900 is that radioactive waste can be minimized because the systems provided efficient fluid delivery where no significant residual amount of a radioactive drug left within system 900.

Table 1 provides a list of some radiopharmaceuticals that may be delivered using a system of this invention.

TABLE 1

| Radiopharmaceutical | Trade Name | Primary Uses |
|---|---|---|
| Cobalt-57 cyanocobalamin | Rubratope; Dicopac | Schilling test |
| Cobalt-58 cyanocobalamin | Dicopac | Schilling test |
| Chromium-51 sodium chromate | Chromotope | for labeling RBCs |
| Flourine-18 FDG | | positron emission tomography imaging |
| Gallium-67 | Neoscan | soft-tissue tumor and inflammatory process imaging |
| Indium-111 chloride | Indiclor | for labeling monoclonal antibodies and peptides (OncoScint &Octreoscan) |
| Indium-111 pentetate (DTPA) | | imaging of CSF kinetics |
| Indium-111 oxyquinoline (oxine) | | for labeling leukocytes and platelets |
| Indium-111 Capromab pendetide | ProstaScint | monoclonal antibody for imaging prostate cancer |
| Indium-111 Imciromab pentetate | Myoscint | monoclonal antibody for diagnosis of myocardial necrosis |
| Indium-111 pentetreotide | Octreoscan | imaging of neuroendocrine tumors |
| Indium-111 satumomab pendetide | OncoScint CR/OV | imaging of metastatic disease associated with colorectal and ovarian cancer |
| I-123 sodium iodide | | thyroid imaging &uptake |
| I-125 iothalamate | Glofil | measurement of glomerular filtration |
| I-125 human serum albumin (RISA) | Isojex | plasma volume determinations |
| I-131 sodium iodide | | thyroid uptake, imaging, & therapy |
| I-131 iodohippurate | Hippuran; Hipputope | renal imaging and function studies |
| I-131 iodomethylnorcholesterol (NP-59) | | adrenal imaging |
| I-131 metaiodobenzylguanidine (MIBG) | I-131 MIBG | imaging of pheochromocytomas and neuroblastomas |
| Krypton-81m gas (from Rb-81 generator) | | pulmonary ventilation imaging |
| P-32 chromic phosphate | Phosphocol ® P32 | therapy of intracavitary malignancies |
| P-32 sodium phosphate | | therapy of polycythemia vera |
| Rubidium-82 (from Sr-82/Rb-82 generator) | Cardio-Gen-82 | positron emission tomography imaging |
| Samarium-153 Lexidronam (Sm-153 EDTMP) | Quadramet | palliative treatment of bone pain of skeletal metastases |
| Strontium-89 | Metastron | palliative treatment of bone pain of skeletal metastases |
| Tc-99m pertechnetate | | imaging of thyroid, salivary glands, ectopic gastric mucosa, parathyroid glands, dacryocystography, cystography |

TABLE 1-continued

| Radiopharmaceutical | Trade Name | Primary Uses |
|---|---|---|
| Tc-99m Apcitide | AcuTect | peptide imaging DVT |
| Tc-99m Arcitumomab | CEA-Scan | monoclonal antibody for colorectal cancer |
| Tc-99m albumin colloid | Microlite - no longer on market | imaging of RES (liver/spleen) |
| Tc-99m bicisate (ECD) | Neurolite | cerebral perfusion imaging |
| Tc-99m Depreotide | Neotect | somatostatin receptor-bearing pulmonary masses |
| Tc-99m disofenin (DISIDA) | Hepatolite | hepatobiliary imaging |
| Tc-99m exametazine (HMPAO) | Ceretec | cerebral perfusion imaging |
| Tc-99m Gluceptate | Glucoscan | renal imaging |
| Tc-99m Human Serum Albumin (HSA) | | imaging of cardiac chambers |
| Tc-99m Lidofenin (HIDA) | Technescan ® HIDA | hepatobiliary imaging |
| Tc-99m Macroaggregated Albumin (MAA) | Pulmolite; Macrotec | pulmonary perfusion |
| Tc-99m Mebrofenin | Choletec | hepatobiliary imaging |
| Tc-99m Medronate (MDP) | | bone imaging |
| Tc-99m Mertiatide | Technescan MAG3 | renal imaging |
| Tc-99m Nofetumomab Merpentan NR-LU-10 | Verluma | monoclonal antibody Fab fragment for imaging small cell lung cancer |
| Tc-99m Oxidronate (HDP) | Osteoscan HDP | bone imaging |
| Tc-99m Pentetate (DTPA) | Techneplex, Technescan DTPA | renal imaging and function studies; radioaerosol ventilation imaging |
| Tc-99m Pyrophosphate (PYP) | | avid infarct imaging |
| Tc-99m Red Blood Cells (RBCs) | Ultratag | imaging of GI bleeds, cardiac chambers |
| Tc-99m Sestamibi | Cardiolite Miraluma | myocardial perfusion imaging breast tumor imaging |
| Tc-99m Succimer (DMSA) | | renal imaging |
| Tc-99m Sulfur Colloid (SC) | | imaging of RES (liver/spleen), gastric emptying, GI bleeds |
| Tc-99m Teboroxime | Cardiotec | myocardial perfusion imaging |
| Tc-99m Tetrofosmin | Myoview | myocardial perfusion imaging |
| Thallium-201 | | myocardial perfusion imaging; parathyroid & tumor imaging |
| Xenon-133 | | pulmonary ventilation imaging |

Figure 15:
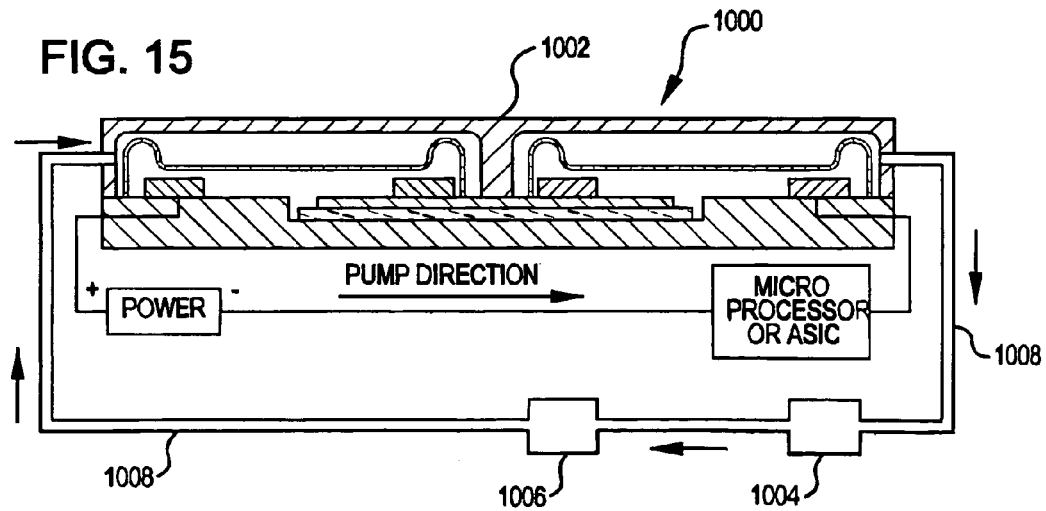
FIG. 15 illustrates a schematic view of one embodiment of an EK sampling system.

FIG. 15 illustrates yet another aspect of the invention, specifically an EK sampling system 1000, which can be adapted to draw, analyze and/or store (within the system) a physiological fluid, such as blood (e.g., for glucose monitoring) or other body fluid containing a target analyte from a patient. In this embodiment, sampling system 1000 comprises an indirect EK pump 1002, which is coupled to a sampler 1004 and a analyzer 1006, which are fluidly coupled to EK pump 1002 via external fluid loop 1008. During use, pump can be operated to effect transport of a physiological fluid taken from a patient by sampler 1004 to analyzer 1006 where the physiological fluid may be evaluated for the analyte. In one example, the Ringers solution, saline or other appropriate fluid can be pumped through fluid loop 1008 where the solution can be mixed with the extracted physiological fluid at sampler 1004 and transported to analyzer 1006.

Sampler 1004 may be any conventionally known system or device for obtaining a physiological fluid. In one embodiment, sample 1004 may comprise a EK pump adapted to hydraulically draw a physiological fluid from a patient. One embodiment of an EK pump system and pump configuration suitable for such an application is described with reference to FIGS. 13a-13b. Likewise analyzer 1006 may be any conventionally known system for testing the obtained sample. For example, analyzer 1006 can be reagent system for determination of a patient's glucose concentrations in the sampled physiological fluid, as further described in U.S. Pat. Nos. 3,298,789, and 3,630,957, the entire contents of which are hereby incorporated by reference.

Figure 16:
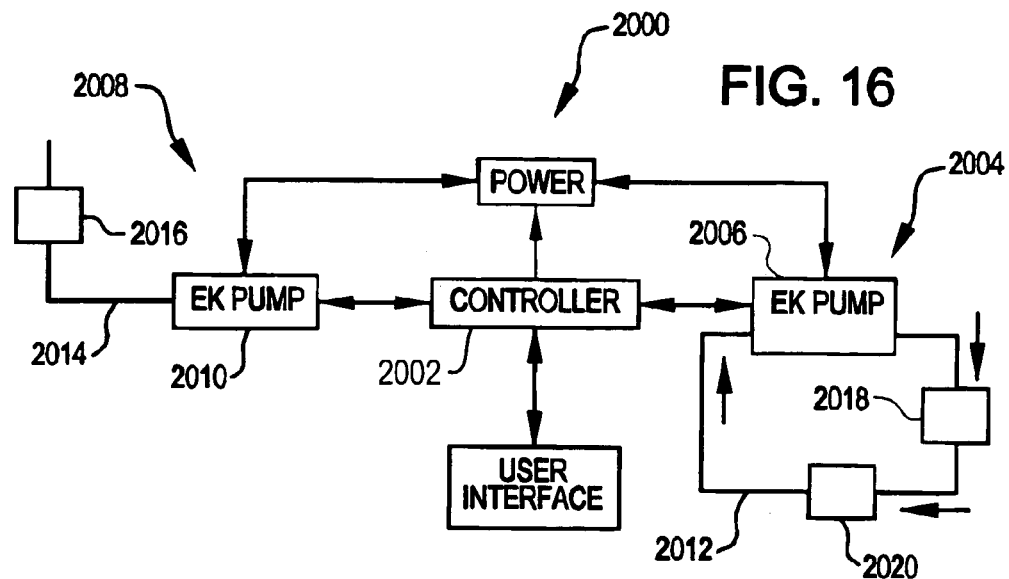
FIG. 16 illustrates a system block diagram of a dual drug delivery and sampling system.

FIG. 16 illustrates a system block diagram of another embodiment, wherein the EK system 2000 is a dual analyte sampling and drug delivery system. In this example, system 2000 broadly comprises a system controller 2002; an analyte sampling subsystem 2004 comprising a first EK pump 2006; and a drug delivery subsystem 2008 comprising a second EK pump 2010. The system controller 2002 serves to control the operation of the sampling and delivery subsystems 2004 and 2008 by controlling voltage being applied to the EK pumps.

In a preferred embodiment, system 2000 comprises two separate fluid paths 2012 and 2014. Fluid path 2014 is coupled the second EK pump 2010 and adapted to electro-osmotically pump a drug from within drug reservoir 2016 to a patient. Fluid path 2012 is coupled to the first EK pump 2006 and adapted to electro-osmotically pump a physiological fluid from sampler 2018 to analyzer 2020 where it can be evaluated. However, while the fluid paths are preferably configured to be separate, the control of drug delivery subsystem 2008 by controller 2002 is based on feedback from sampling subsystem 2004. Controller 2002 is adapted to send and/or receive data to and from the sampling and drug delivery subsystems 2004 and 2008 to modulate drug delivery and determine an appropriate drug delivery profile or regime depending on monitoring and analysis of a patient's physiological and/or chemical state by sampling subsystem 2004.

As will be appreciated by those skilled in the art, in this embodiment, the sampling subsystem 2004 can be configured to measure a specific analyte and/or a change in analyte parameter and to compare it to a known values stored within a memory component of controller 2002, so that the EK system 2000 can effect drug delivery in response to any physiological, physiochemical or chemical changes in a patient. In one example, depending on input from the sampling subsystem 2004, controller 2002 can execute a command signal to the delivery subsystem 2008 to initiate, control and/or terminate of an operation.

For example, system 2000 can be configured for the treatment of diabetes and adapted to deliver insulin. Insulin delivery can be initiated after a patient's blood glucose concentration has been determined by sampling subsystem 2004. Delivery subsystem 2008 can be configured to deliver a quantity of insulin into the patient in response to the determined blood glucose concentration. Delivery of insulin in response to the determined blood glucose concentration may comprise automatically effecting delivery of insulin or can be configured to require user initiation of insulin delivery or both. In addition, delivery subsystem can be adapted to deliver more than one type of insulin, insulin at different delivery rates to effect basal and bolus delivery. In addition, the system can be adapted to deliver a frequent micro-volumes or microboluses of insulin in order to maintain a constant glucose concentrations in a patient to effect better or effective diabetes management.

Figure 17:
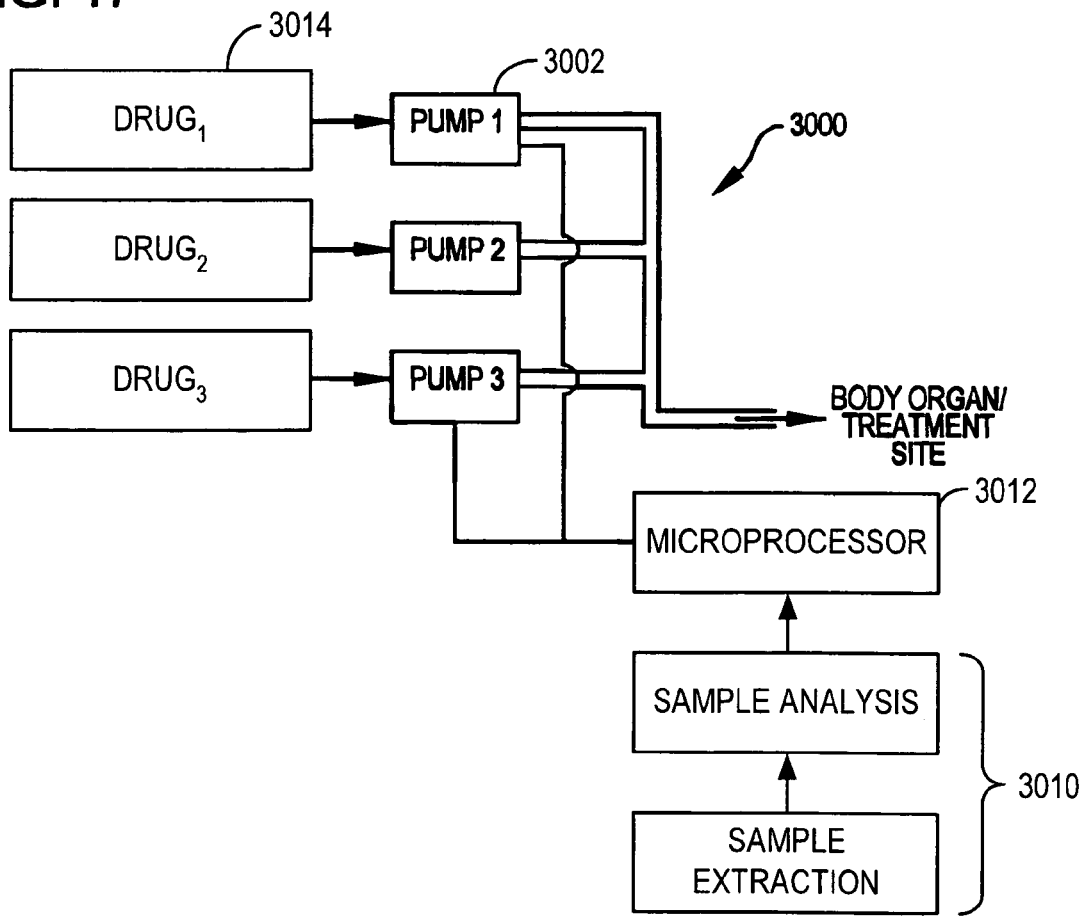
FIG. 17 illustrates system block diagram of a multi-drug delivery and sampling system.
Figure 18:
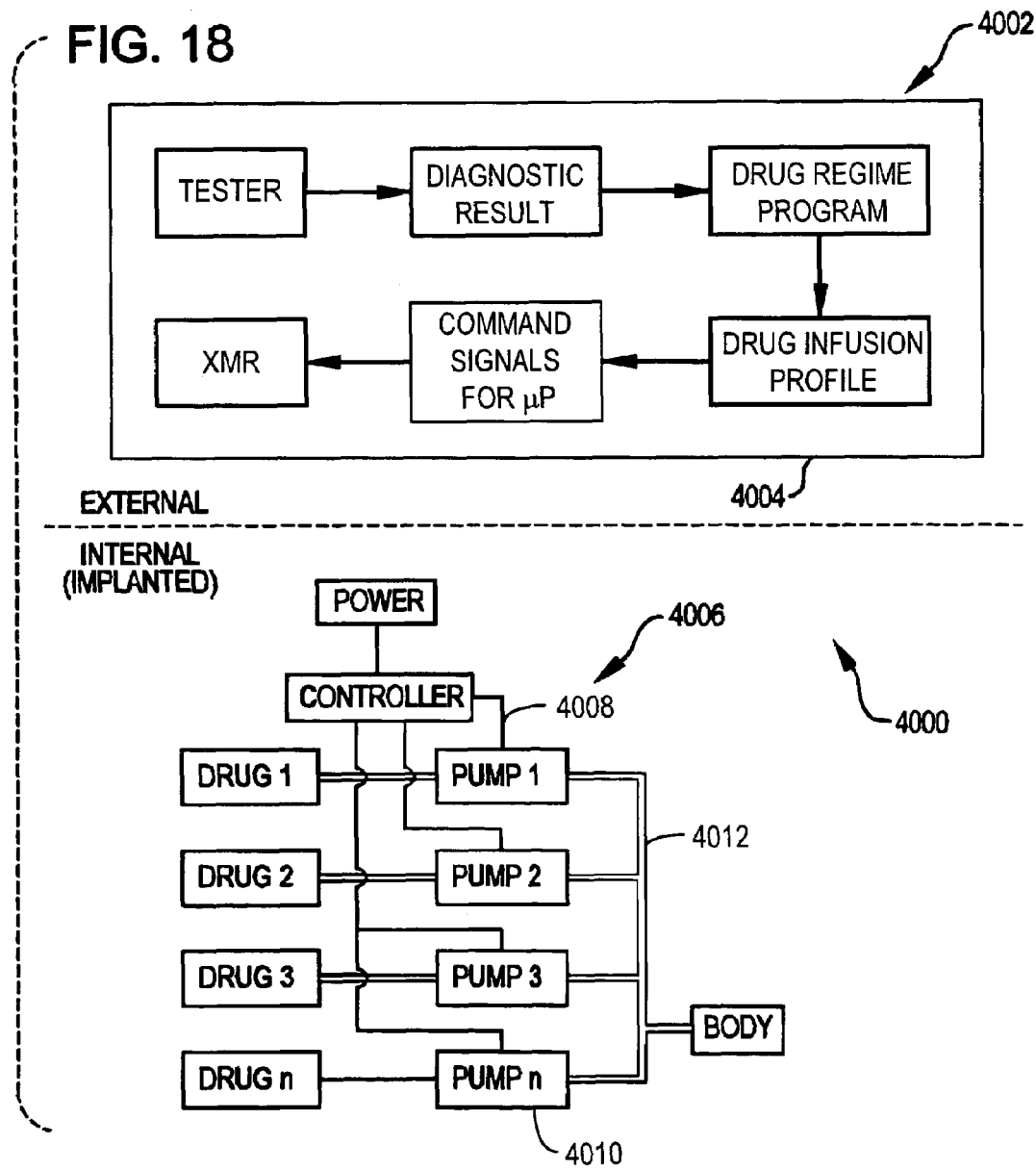
FIG. 18 illustrates a system block diagram of a multi-drug, multi-pump externally controllable delivery system.
Figure 19:
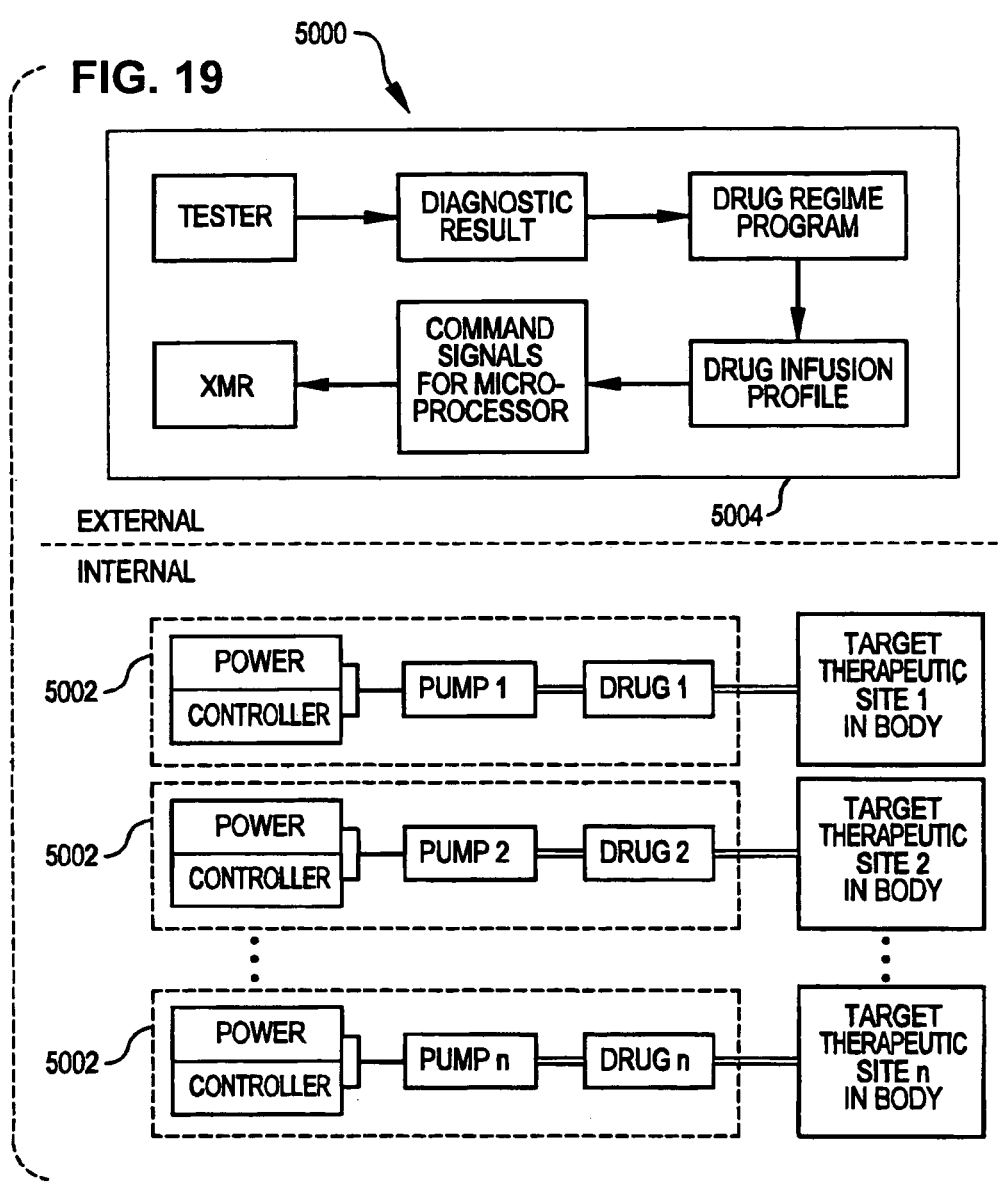
FIG. 19 illustrates a system block diagram of a distributed, multi-drug, multi-pump externally controllable delivery system.

In yet another embodiment, the various systems and pumps provided herein may be multiplexed to provide delivery of more than one drug, comprise more than one fluid path, flow rate or EK pump as schematically depicted in FIGS. 17-19. For example, FIG. 17 illustrates a system block diagram for a multi-pump, multi-reservoir drug delivery system 3000. In this embodiment, the various EK pumps of the invention may be multiplexed and adapted to provide a system capable of delivering more than one drug $D_1 \ldots D_n$, for example, in order to deliver a drug cocktail or for delivering one or more drugs at differing flow rates $FR_1 \ldots FR_n$, or for delivering one drug at differing flow rates (e.g., for basal, bolus delivery) or the like.

In one embodiment, for example, EK system 3000 can be adapted to deliver more than one compound, to mimic or functionally augment or replace diseased or organ, such as a pancreas. In this example, drug delivery subsystem can comprise one or more EK delivery pumps 3002 that can be configured to deliver one or more compounds or drugs (e.g., trypsin, steapsin, amylolytic ferment) and which are coupled to a sampling subsystem 3010 for providing feedback control of the multi-pump delivery subsystem 3012 (through, e.g., diagnostics sampling blood or other biological fluids) controlling how much of each substance is needed. Other organs may be mimicked or augmented in this way. Alternatively, system 3000 can be configured to deliver a single drug from drug reservoir 3014 which is common to all pumps 3002, for delivery at differing flow rates, etc., FIG. 18 illustrates yet another embodiment of a multi-reservoir, multi-pump drug delivery system 4000 comprising an external controller 4002. Operation of the implanted delivery system 4000 can be operationally controlled by external controller 4002 having a user interface 4004. Signals (such as RF, IR or other electronic transmissions) between external controller and implanted delivery system 4000 are provided to allow interface with, and/or control, by external controller 4002 of one or more of the components of the delivery system 4006 such as a controller, battery, electrodes, feedback sensors, etc. Signal transmission lines 4008 illustrate one method of controlling the multiple pumps 4010 system 4000. In this embodiment, the fluid paths 4012 of system 4000 are illustrated. As shown, the various fluids (e.g., drugs) can be combined for delivery to a target treatment site inside a body. Alternatively, an external pump or pumps located outside of the patient may be remotely controlled to deliver one or more fluids to the patient.

As will be appreciated by one skilled in the art, this embodiment may be useful for medical applications where the delivery of multiple agents is required, e.g., for diagnostic imaging studies, for cancer treatment where multiple chemotherapeutic agents need to be delivered simultaneously or in a particular timing or order, where one agent counteracts unwanted side effects of another agent, etc., For example, Agent A is a chemotherapy cocktail called Taxotere used in early or late stage breast cancer. The unwanted side effect is a reduction in white blood cells. Agent B is an antibiotic that is provided in proportion to the reduction in white blood cell activity or white blood cell count. Agent B could be provided at a first, higher rate immediately following the highest dosage of chemotherapy, then tapered off as the body's ability to produce white blood cells improves or is restored.

Other examples include a multi-drug cocktail to treat AIDS (reservoirs contain AZT, reverse transcriptase inhibitors and protease inhibitors) and multi-drug cocktails to treat tuberculosis, hepatitis B, hepatitis C, and tissue rejection after an organ transplant.

Generally, because of their small size, and because they may be formed in a variety of shapes, the EK pumps of this invention may be implanted in proximity to the portion of a body being treated by the agent delivered by the pump: For example, the pump may have a form factor adapted to the shape of the liver and may be implanted to treat hepatitis B. Other potential organs include the kidneys, the gall bladder, etc., FIG. 19 is a system block diagram of an implantable "distributed" drug delivery system 5000 comprising one or more implantable drug delivery subsystems 5002 and an external controller 5004. As illustrated, the various delivery subsystems 5002 can be implanted at different locations inside a patient's body for drug delivery at more than one treatment site. In this embodiment, each of the subsystems 5002 is configured to be operable by external controller 5004. Alternatively, an external pump or pumps located outside of the patient may be remotely controlled to deliver one or more fluids to the patient.

Other embodiments of indirect pumps may be provided. For example, instead of using a diaphragm or syringe to isolate a reservoir, the drug or other fluid to be delivered may be loaded into a collapsible bag placed within a rigid chamber. Delivery of the EK pump fluid into the portion of the rigid chamber outside the bag collapses the bag to dispense the drug out through an outlet, such as a plastic tube. This approach may be used to deliver high viscosity drugs, for example.

In addition, dried (e.g., lyophilized) versions of drugs may be preloaded into the pump's drug delivery reservoir for shipment and storage of the pump and drug, then reconstituted immediately prior to use.

Pumping system embodiments of the present invention may include electronics and communications that allow for various level of control authority, for example the prescribing physician may have a greater authority over dosing, while the patient has a lesser authority. This authority my include electronic key authentication for granting such authority as well as for activation (e.g., for cases where the device dispenses controlled substances requires specific license to prescribe/distribute, such as for a scheduled narcotic). As another example, the device can be configured to deliver only a total amount of drug over a period of time, regardless of how much drug is delivered at each of one or more times during that period. Alternatively, the device can be controlled to operate for only a set period of time, no matter how much drug has been delivered. The device can also provide a display showing the amount of drug remaining in the reservoir, the amount of dose delivered at one time or overall, etc., Other manners of automatic feedback control of the EK pumps of this invention may be provided. For example, physiological inputs, such as limb movement during Parkinson's-induced tremor or epileptic seizure, may trigger the release of a drug from the EK pump to treat the condition.

The device may include electronics and communications that provide for making a historical record of device operation that may be complemented with records of various physiological responses or conditions (e.g., heart rate, blood pressure, EKG, blood gases, serum levels of specific compounds). These records can be downloaded for analysis and use in optimizing treatment and/or judging response to treatment. Various levels of authority can be included if desired to allow some, all or none of the download features.

Figure 20:
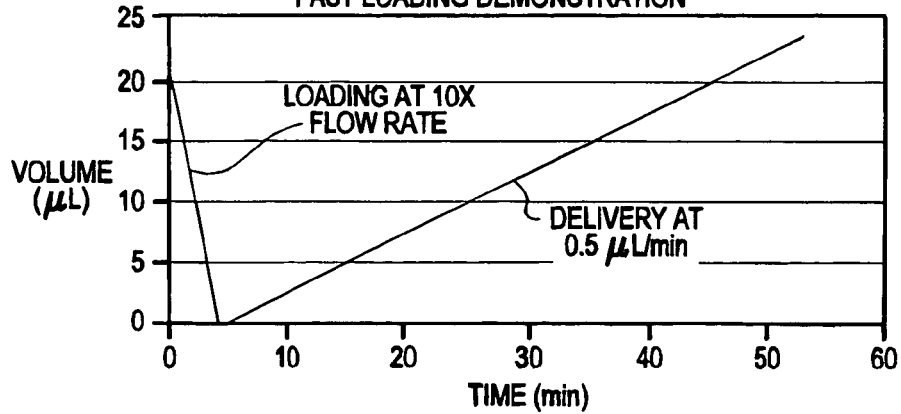

FIGS. 20-23 are provided to illustrate the performance aspects of the EK systems and pumps provided herein. For example, FIG. 20 is provided to illustrate fast loading and delivery flow rates plotted over time for a typical EK pump in accordance with the present invention. As illustrated it is possible to configure the various EK pumps and systems to provide fast loading and delivery of a pump fluid to effect transport and movement of fluid out of or through an EK fluid system.

Figure 21:
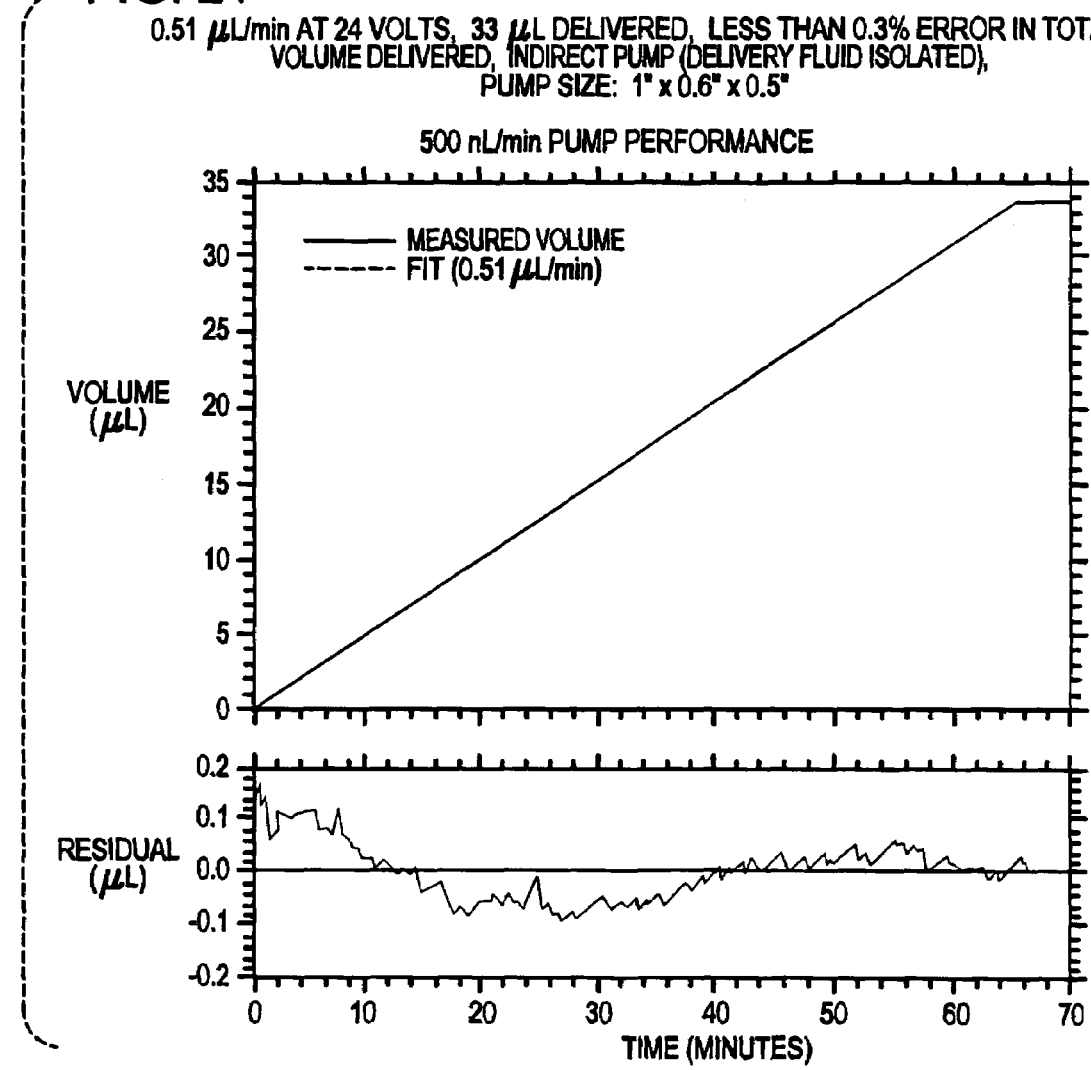
Figure 22:
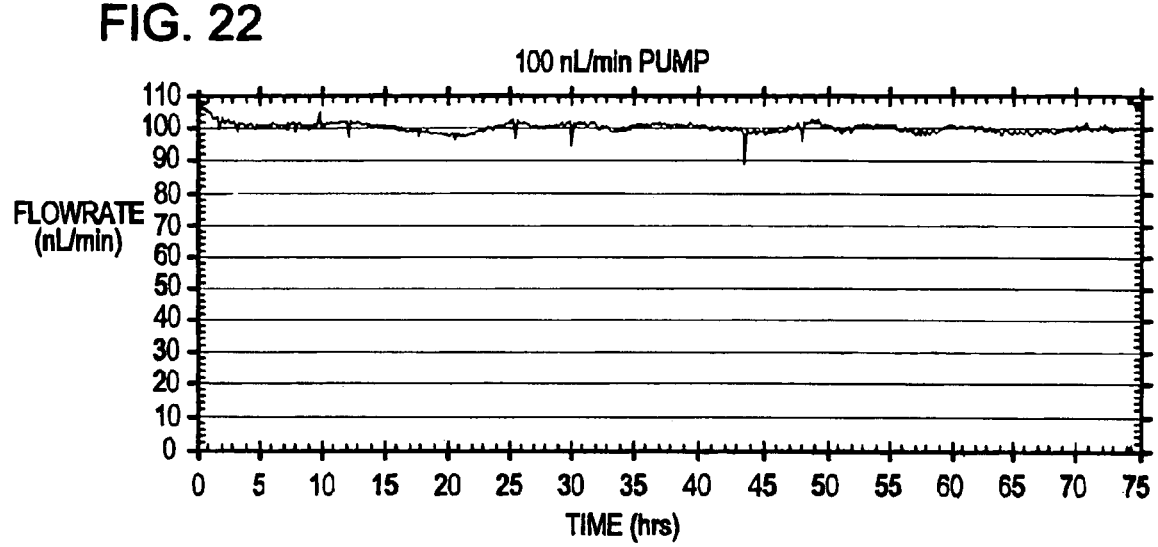
Figure 23:
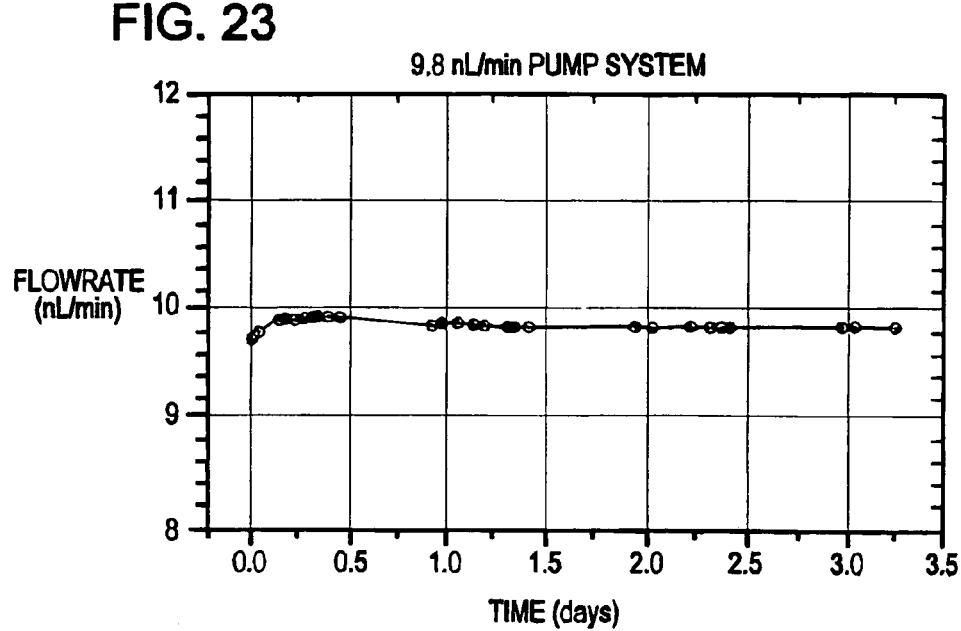

FIG. 21 is provided to illustrate the overall reliability and precision of fluid transport by the EK pumps of the present invention. In this example, constant fluid flow rates can be maintained during pump operation, little or no error in flow rates at any given time. As previously described above, by employing certain techniques (e.g., controlled release of and uptake of ions in the pump fluid, controlling the voltage applied below a pump fluid voltage potential, careful selection of electrode materials), flow rate errors can be maintained at less than 5% during steady-state flow. FIGS. 22 and 23 are provided to illustrate the constant and precise steady-state flow rate can be maintained over a period of hours or over a period of days as may be required.

Pumps of the present invention may be advantageously used to dispense agents of wide ranging physical characteristics. For example, embodiments of the present invention may be used to pump agents having a viscosity of 10 to 100 poise, 100 to 1,000 poise or 1,000 to 10,000 poise. In each of these various viscosity ranges, pumps of the present invention maintain the precision and micro-delivery aspects described herein. For example, pumps of the present invention may provide 1-10 microliters per hour flow rates for agents ranging from 10 to 10,000 poise.

The EK pump systems of this invention may be used to deliver many different drugs or other substances to treat a variety of disorders. For example, in a patient diagnosed with a disorder in the autonomic and/or somatic motor nervous systems or whose treatment requires agent or agents that have a therapeutic effect on the autonomic and/or somatic motor nervous systems, the agent (or agents in a co-treatment embodiment) dispensed by the pump may include by way of illustration and not limitation: muscarinic receptor agonists and antagonists; anticholinesterase agents; agents acting at the neuromuscular junction and/or autonomic ganglia; catecholamines, sympathominmetic drugs, and adrenergic receptor antagonists; and 5-hydroxytryptamine (5-HT, serotonin) receptor agonists and antagonists.

In a patient diagnosed with a disorder in the central nervous system (CNS) or whose treatment requires agent or agents that have a therapeutic effect on the central nervous system and/or act at synaptic and/or neuroeffector junction sites, the agent dispensed by the pump may include by way of illustration and not limitation: general anesthetics, local anesthetics, analogs of benzodiazepine and barbiturates, a hypnotic, a sedative, aliphatic alcohols, ethanol, nonbenzodiazepine sedative-hypnotic drugs, sedative-hypnotic agents of diverse chemical structure (e.g., paraldehyde, chloral hydrate), CNS depressants, antidepressant therapeutic agents, antipsychotic and antimanic agents, norepinephrine inhibitors, monoamine oxidase inhibitors, selective serotonin-reuptake inhibitors, benodiazepine sedative-antianxiety agents, serotonin $5-HT_{1A}$-receptor partial agonists, buspirone, agents that block $D_2$-dopamine receptors, agents that reduce dopamine neurotransmission in forebrain, tricyclic phenothiazines, thioxanthenes, dibenzepines, butyrophenones and congeners, heterocyclics, benzamides, agents that interact with $D_1$- and $D_4$-dopaminergic, $5-HT_{2A}$- and $5-HT_{2C}$-serotonergic, and α-adrenergic receptors, clozapine, olanzapine, quetiapine, risperidone, fluphenazine, haloperidol, chlorpromazine, lithium, lithium carbonate, lithium citrate, sedative-anticonvulsant benzodiazepines, sodium divalproex, carbamazepine, antiseizure drugs that promote an inactivated state of voltage-activated Na+ channels, antiseizure drugs that enhance gamma-aminobutyric acid (GABA)-mediated synaptic inhibition, antiseizure drugs that enhance gamma-aminobutyric acid (GABA)-mediated synaptic inhibition by an action presynaptically, antiseizure drugs that enhance gamma-aminobutyric acid (GABA)-mediated synaptic inhibition by an action postsynapically, cholinergic agents, levodopa, dopamine-receptor agonists, catechol-O-methyltransferase (COMT) inhibitors, acetylcholinesterase (ACHE) inhibitors, NMDA-receptor antagonists, and opioid analgesics.

In a patient having a condition, such as injury or inflammation, causing a physiological or pathophysiological response to the condition or whose treatment requires agent or agents that have a therapeutic effect on the physiological or pathophysiological response to injury or inflammation, the agent (or agents in a co-treatment embodiment) dispensed by the pump may include by way of illustration and not limitation: histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteriodal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, and leukotriene inhibitors.

In a patient diagnosed with a disorder affecting renal and/or cardiovascular function or whose treatment requires agent or agents that have a therapeutic effect on the renal and/or cardiovascular function, the agent (or agents in a co-treatment embodiment) dispensed by the pump may include by way of illustration and not limitation: diuretics, vasopressin, agents affecting the renal conservation of water, rennin, angiotensin, agents useful in the treatment of myocardial ischemia, antihypertensive agents, angiotensin converting enzyme inhibitors, β-andrenergic receptor antagonists, agents for the treatment of hypercholesterolemia, and agents for the treatment of dyslipidemia.

In a patient diagnosed with a disorder in the gastrointestinal system and/or function or whose treatment requires agent or agents that have a therapeutic effect on the gastrointestinal system or function, the agent (or agents in a co-treatment embodiment) dispensed by the pump may include by way of illustration and not limitation: agents used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used, for pancreatic disease.

In a patient diagnosed with a disorder requiring chemotherapy of a parasitic infection or whose treatment requires agent or agents that have a chemotherapeutic effect on an infection in the patient, the agent (or agents in a co-treatment embodiment) dispensed by the pump may include by way of illustration and not limitation: drugs used to treat protozoal infections, drugs used to treat Malaria, Amebiasis, Giardiasis, Trichomoniasis, Trypanosomiasis, and/or Leishmaniasis, and/or drugs used in the chemotherapy of helminthiasis.

In a patient diagnosed with a disorder requiring chemotherapy of neoplastic diseases or whose treatment requires agent or agents that have a chemotherapeutic effect on a neoplastic disease or infection in the patient, the agent (or agents in a co-treatment embodiment) dispensed by the pump may include by way of illustration and not limitation: antineoplastic agents.

In a patient diagnosed with a disorder requiring chemotherapy of microbial diseases or whose treatment requires agent or agents that have a chemotherapeutic effect on microbial diseases or infections in the patient, the agent (or agents in a co-treatment embodiment) dispensed by the pump may include by way of illustration and not limitation: antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents. Additional disorders requiring chemotherapy or whose treatment requires agent or agents that have a chemotherapeutic effect in the patient are described in the Handbook of Chemotherapy (Sixth Edition), Roland T. Skeel, M.D. Editor, Physicians Cancer Chemotherapy Drug Manual 2003 by Edward Chu, Vincent T. DeVita, Lippincott's Cancer Chemotherapy Handbook by Delia C. Baquiran, Jean Gallagher, each of which is incorporated herein by reference in their entirely and for all purposes.

In addition, agents may include drugs used for immunomodulation, such as immunomodulators, immunosuppressive agents, tolerogens, and immunostimulants.

In addition, agents may include drugs acting on the blood and the blood-forming organs, hematopoietic agents, growth factors, minerals, and vitamins, anticoagulant, thrombolytic, and antiplatelet drugs.

In addition, agents may include hormones and hormone antagonists, pituitary hormones and their hypothalamic releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, and other compounds.

In addition, agents may include vitamins such as water-soluble vitamins, vitamin B complex, ascorbic acid, fat-soluble vitamins, vitamins A, K, and E. In addition, agents may include drugs suited to dermatological pharmacology and ocular pharmacology.

Additional disorders and their treatments may be found in Goodman and Gilman's "The Pharmacological Basis of Therapeutics" Tenth Edition edited by Hardman, Limbird and Gilman or the Physician's Desk Reference, both of which are incorporated herein by reference in their entirety. It is to be appreciated therefore that the embodiments of the present invention are not limited merely to the agent, agents or disorders listed above but that embodiments of the present invention may be used to advantage for the delivery of agents, including diagnostic and testing agents for the purpose of detecting, treating, managing, or diagnosing any of the above listed disorders as well as those disorders mentioned in Goodman and Gilman's "The Pharmacological Basis of Therapeutics" Tenth Edition edited by Hardman, Limbird and Gilman or mentioned in the Physician's Desk Reference.

Agents may be used alone or in formulations comprising a pharmaceutically acceptable carrier. The formulation may also comprise a solvent. The agent may be a biological molecule or a pharmaceutical drug, DNA, RNA or a protein.

It is to be appreciated that the EK functionality of pumps of the present invention do not provide any perceptible indication of operation. As used herein, perceptible indication of operation refers to a any outward sign that the pump is operating. For example, conventional piezoelectric pumps have a distinct buzz resulting from the vibration of the piezoelectric elements. Conventional mechanical and peristaltic pumps have distinct mechanical noises that indicate the pump is operating. Such perceptible indications, especially noises, are undesirable for pump systems worn on the person or to be operated in public, for example, to dispense insulin prior or during a meal. Embodiments of the present invention are capable of dispensing or administering an agent without a perceptible indication of pump operation. For example, embodiments of the present invention may operate and generate noise levels below 20 db, or in some embodiments below 10 db or in still other embodiments generate noise inaudible or barely audible to a human being.

The pump and pumping systems described herein are useful in methods for the treatment of animal subjects. The term "animal subject" as used herein includes humans as well as other mammals. The methods generally involve the administration of one or more agents for the treatment of one or more diseases. Combinations of agents can be used to treat one disease or multiple diseases or to modulate the side-effects of one or more agents in the combination.

The term "treating" and its grammatical equivalents as used herein includes achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For example, administration of a chemotherapeutic agent to a patient suffering from cancer provides therapeutic benefit not only when the patient's tumor marker level is decreased, but also when an improvement is observed in the patient with respect to other complications that accompany the cancer like pain and psychiatric disorders. For prophylactic benefit, the combination of phosphate binder and gastric pH modulator may be administered to a patient at risk of developing a particular disease, like cancer, or to a patient reporting one or more of the physiological symptoms of a disease, even though a diagnosis of this disease may not have been made.

In some of the embodiments of the present invention the agent is a drug. Drugs are any compounds of any degree of complexity that perturb a biological state, whether by known or unknown mechanisms and whether or not they are used therapeutically. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; pesticides; herbicides; and insecticides. The biological effect of a drug may be a consequence of, inter alia, drug-mediated changes in the rate of transcription or degradation of one or more species of RNA, the rate or extent of translation or post-translational processing of one or more polypeptides, the rate or extent of the degradation of one or more proteins, the inhibition or stimulation of the action or activity of one or more proteins, and so forth. In fact, most drugs exert their affects by interacting with a protein. Drugs that increase rates or stimulate activities or levels of a cellular constituent are called herein "activating drugs", while drugs that decrease rates or inhibit activities or levels of cellular constituents are called herein "inhibiting drugs".

The agents used in the pumps described herein may be used alone or in combination with one or more pharmaceutically acceptable carrier. Examples of suitable carriers are known in the art, for example, see Remington: The Science and Practice of Pharmacy by A. R. Gennaro (Editor), 20$^{th}$ Edition, 2000. Preferably the carrier improves the delivery of the agent to the subject. It is also preferable that the carrier does not hinder the delivery of the agent. In some of the embodiments, the carrier has sufficient ionic properties to support the electro-osmotic functioning of the pump.

In some embodiments, the pump is used to detect the presence of one or more markers of a disease. If a marker of a disease is detected as being present, the pump is used to deliver one or more agents to treat the disease. The term marker as used herein is intended to encompass biological markers and also measurable phenotypic characteristics like temperature, pressure, etc., Examples of biological markers include, but are not limited to, DNA, RNA, proteins, enzymes, hormones, cells, portions of cells, tissues, or organs, subcellular organelles like mitochondria, nucleus, Golgi complex, lysosome, endoplasmic reticulum, and ribosome, chemically reactive molecules like $H^+$, superoxides, and ATP. Examples of markers include, but are not limited to, prostate specific antigen for prostate cancer, glucose and/or insulin levels for diabetes, and blood pressure measurements for hypertension.

While preferred embodiments of the present invention have been shown and described herein, it will be obvious to one skilled in the art that such embodiments are provided by way of example only. Numerous variations, changes, and substitutions will now occur to those skilled in the art without departing from the invention. For example, the systems of the invention may comprise for example any of the features of conventional drug delivery or analyte monitoring devices including for example alarms or other indicators for notifying a user of when drug delivery is complete. In yet another example, various retention members and the like may be coupled to the various device and systems in aid in the portability of the various devices and system. In addition, the intended uses of the present invention include a variety of medical applications as well as other applications where highly precise, compact devices for fluid transport are needed. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of pumping fluid comprising:
providing an electrokinetic pump comprising a pair of double-layer capacitive electrodes having a capacitance of at least $10^{-2}$ Farads/cm$^2$ and being connectable to a power source, a porous dielectric material disposed between the electrodes and a reservoir containing pump fluid;
connecting the electrodes to a power source; and
moving pump fluid out of the reservoir substantially without the occurrence of Faradaic processes in the pump.

2. The method of claim 1 wherein the electrodes comprise high microscopic surface area electrodes.

3. The method of claim 1 wherein the moving step further comprises moving the pump fluid out of the reservoir and through a pump outlet.

4. The method of claim 1 wherein the reservoir comprises a first reservoir, the electrokinetic pump further comprising a second reservoir, the moving step comprising moving the pump fluid out of the first reservoir into the second reservoir.

5. The method of claim 4 wherein the electrokinetic pump further comprises a third reservoir and a sampled fluid disposed in the third reservoir, the moving step further comprising moving sampled fluid through a pump inlet into the third reservoir as the pump fluid moves from the first reservoir into the second reservoir.

6. The method of claim 4 wherein the electrokinetic pump further comprises a third reservoir and a dispensed fluid disposed in the third reservoir, the moving step further comprising moving dispensed fluid out of the third reservoir and through a pump outlet as the pump fluid moves from the first reservoir into the second reservoir.

7. The method of claim 6 wherein the step of moving the pump fluid comprises moving the pump fluid at a pump fluid flow rate and the step of moving the dispensed fluid comprises moving the dispensed fluid at a dispensed fluid flow rate, the dispensed fluid flow rate being between about 0.1 times and 10 times the pump fluid flow rate.

8. The method of claim 6 wherein the providing step comprises providing an electrokinetic pump having a volume no greater than 250% of an initial volume of dispensed fluid.

9. The method of claim 6 wherein the third reservoir comprises a syringe, the moving step further comprising moving the dispensed fluid out of the syringe and into a patient as the pump fluid moves from the first reservoir into the second reservoir.

10. The method of claim 9 further comprising adding dispensed fluid to the syringe prior to the moving step.

11. The method of claim 6 wherein the third reservoir comprises a collapsible container, the moving step further comprising moving the dispensed fluid out of the collapsible container and into a patient as the pump fluid moves from the first reservoir into the second reservoir.

12. The method of claim 6 wherein the electrokinetic pump comprises a first electrokinetic pump and the moving step comprises moving dispensed fluid into a patient, the method further comprising:
providing a second electrokinetic pump comprising a pair of double-layer capacitive electrodes connectable to a power source, a porous dielectric material disposed between the electrodes, a first reservoir of pump fluid, a second reservoir, a third reservoir and a dispensed fluid disposed in the third reservoir;
connecting the electrodes of the second electrokinetic pump to a power source;
moving dispensed fluid out of the third reservoir and through a second electrokinetic pump outlet into the patient as pump fluid of the second electrokinetic pump moves from the first reservoir into the second reservoir of the second electrokinetic pump substantially without the occurrence of Faradaic processes in the second pump.

13. The method of claim 12 wherein the step of moving dispensed fluid from the first electrokinetic pump is performed at a first rate and the step of moving dispensed fluid from the second electrokinetic pump is performed at a second rate different than the first rate.

14. The method of claim 12 wherein the dispensed fluid of the first electrokinetic pump and the dispensed fluid of the second electrokinetic pump are the same kind of fluid.

15. The method of claim 12 wherein the dispensed fluid of the first electrokinetic pump and the dispensed fluid of the second electrokinetic pump are different kinds of fluid.

16. The method of claim 6 wherein the electrokinetic pump comprises a first electrokinetic pump and the moving step comprises moving dispensed fluid into a patient, the method further comprising:
providing a second electrokinetic pump comprising a pair of double-layer capacitive electrodes connectable to a power source, a porous dielectric material disposed between the electrodes, a first reservoir of pump fluid, a second reservoir, a third reservoir and a dispensed fluid disposed in the third reservoir;
connecting the electrodes of the second electrokinetic pump to a power source;
moving dispensed fluid out of the second electrokinetic pump third reservoir and through the pump outlet into the patient as pump fluid of the second electrokinetic pump moves from the first reservoir into the second reservoir of the second electrokinetic pump substantially without the occurrence of Faradaic processes in the second pump.

17. The method of claim 16 wherein the step of moving dispensed fluid from the first electrokinetic pump is performed at a first rate and the step of moving dispensed fluid from the second electrokinetic pump is performed at a second rate different than the first rate.

18. The method of claim 16 wherein the dispensed fluid of the first electrokinetic pump and the dispensed fluid of the second electrokinetic pump are the same kind of fluid.

19. The method of claim 16 wherein the dispensed fluid of the first electrokinetic pump and the dispensed fluid of the second electrokinetic pump are different kinds of fluid.

20. The method of claim 6 wherein the electrokinetic pump comprises a first electrokinetic pump and the moving step comprises moving dispensed fluid into a patient, the method further comprising:
providing a second electrokinetic pump comprising a pair of double-layer capacitive electrodes connectable to a power source, a porous dielectric material disposed between the electrodes, a first reservoir of pump fluid and a second reservoir;
connecting the electrodes of the second electrokinetic pump to a power source;
moving dispensed fluid out of the third reservoir and through the pump outlet into the patient as pump fluid of the second electrokinetic pump moves from the first reservoir into the second reservoir of the second electrokinetic pump substantially without the occurrence of Faradaic processes in the second pump.

21. The method of claim 6 further comprising determining a patient's need for the dispensed fluid, the moving step further comprising dispensing a quantity of the dispensed fluid in response to the determined need.

22. The method of claim 21 wherein the dispensed fluid comprises insulin and the determining step comprises determining the patient's blood glucose concentration, the moving step comprising injecting a quantity of insulin into the patient in response to the determined blood glucose concentration.

23. The method of claim 22 wherein the moving step comprises automatically injecting a quantity of insulin into the patient in response to the determined blood glucose concentration.

24. The method of claim 21 wherein the determining step comprises sampling a fluid taken from the patient with a second electrokinetic pump.

25. The method of claim 6 further comprising monitoring a parameter related to an amount of dispensed fluid moved out of the third reservoir during the moving step.

26. The method of claim 25 further comprising using the monitored parameter to provide feedback control of the moving step.

27. The method of claim 26 wherein the monitored parameter is flow rate.

28. The method of claim 26 wherein the monitored parameter is position of a third reservoir pump element.

29. The method of claim 25 further comprising using the monitored parameter to provide an indication related to the dispensed fluid.

30. The method of claim 25 further comprising using the monitored parameter to calculate a desired amount of dispensed fluid to be dispensed.

31. The method of claim 29 wherein the step of using the monitored parameter comprises using the monitored parameter to indicate the presence of an occlusion in the pump outlet.

32. The method of claim 6 wherein the moving step further comprises moving dispensed fluid out of the third reservoir for a fixed time interval to dispense a fixed volume of dispensed fluid.

33. The method of claim 6 further comprising adjusting an amount of dispensed fluid moved out of the third reservoir.

34. The method of claim 6 further comprising loading the dispensed fluid into the third reservoir and treating the electrokinetic pump to alter a characteristic of the dispensed fluid.

35. The method of claim 34 wherein the treating step comprises irradiating the electrokinetic pump.

36. The method of claim 4 further comprising moving pump fluid from the second reservoir to the first reservoir after the first moving step.

37. The method of claim 1 wherein the moving step comprises moving substantially all of the pump fluid out of the reservoir substantially without the occurrence of Faradaic processes in the pump.

38. The method of claim 37 wherein the moving step comprises moving the pump fluid out of the reservoir at a flow rate of less than about 1 microliter/minute and with a steady state flow rate error of no more than about 5% over the entire method step.

39. The method of claim 1 further comprising generating a pump fluid pressure between about 1 and about 1000 psi.

40. The method of claim 1 wherein the electrokinetic pump further comprises a power source connectable to the electrodes and a housing containing the electrodes, dielectric material, reservoir and power source, the electrokinetic pump having a volume of at most about 11 cm$^3$, the moving step further comprising moving at least about 0.2 milliliters of pump fluid.

41. The method of claim 40 wherein the moving step comprises moving the pump fluid at a rate of less than about 10 nanoliters/min.

42. The method of claim 41 wherein the moving step comprises moving the pump fluid substantially continuously for about 30 days.

43. The method of claim 1 further comprising supporting the electrokinetic pump on a patient.

44. The method of claim 43 further comprising implanting the electrokinetic pump in a patient.

45. The method of claim 43 wherein the electrokinetic pump has a shape, the implanting step comprising placing the electrokinetic pump adjacent to an anatomical feature of the patient having a shape complementary to the electrokinetic pump shape.

46. The method of claim 1 wherein the electrokinetic pump comprises a first electrokinetic pump, the moving step comprising moving pump fluid at a first rate into a patient, the method further comprising:
    providing a second electrokinetic pump comprising a pair of double-layer capacitive electrodes connectable to a power source, a porous dielectric material disposed between the electrodes and a reservoir of a pump fluid;
    connecting the electrodes of the second electrokinetic pump to a power source; and
    moving pump fluid out of the second electrokinetic pump reservoir at a second rate into the patient substantially without the occurrence of Faradaic processes in the second pump.

47. The method of claim 46 wherein the pump fluid of the first electrokinetic pump and the pump fluid of the second electrokinetic pump are the same kind of fluid.

48. The method of claim 46 wherein the pump fluid of the first electrokinetic pump and the pump fluid of the second electrokinetic pump are different kinds of fluid.

49. The method of claim 1 wherein the connecting step comprises connecting the power source to the electrodes in a time modulated manner.

50. The method of claim 1 wherein the connecting step comprises alternating the power source between an on state and an off state.

51. The method of claim 1 wherein the connecting step comprises alternating the power source between a normally off state and a periodic on state in response to a computer program.

52. An electrokinetic pump system comprising:
    a pair of double-layer capacitive electrodes having a capacitance of at least $10^{-2}$ Farads/cm$^2$;
    a porous dielectric material disposed between the electrodes;
    a reservoir containing pump fluid; and
    a power source connected to the electrodes; the electrodes, dielectric material and power source being adapted to move the pump fluid out of the reservoir substantially without the occurrence of Faradaic processes in the pump.

53. The electrokinetic pump system of claim 52 further comprising a pump outlet, the electrodes, dielectric material and power source being further adapted to move the pump fluid out of the reservoir and through the pump outlet.

54. The electrokinetic pump system of claim 52 wherein the reservoir is a first reservoir, the system further comprising a second reservoir, the electrodes, dielectric material and power source being further adapted to move the pump fluid out of the first reservoir and into the second reservoir.

55. The electrokinetic pump system of claim 54 further comprising a third reservoir containing dispensed fluid and a pump outlet, the electrodes, dielectric material and power source being further adapted to move the dispensed fluid out of the pump outlet as the pump fluid moves from the first reservoir into the second reservoir.

56. The electrokinetic pump system of claim 55 further comprising an indicator adapted to indicate an amount of dispensed fluid present in the third reservoir.

57. The electrokinetic pump system of claim 55 further comprising a controller adapted to control delivery of power from the power source to the electrodes to move a fixed volume of dispensed fluid out of the third reservoir.

58. The electrokinetic pump system of claim 55 further comprising a controller adapted to control delivery of power from the power source to the electrodes to move dispensed fluid for a fixed period of time.

59. The electrokinetic pump system of claim 55 further comprising a controller adapted to control delivery of power from the power source to the electrodes to move dispensed fluid out of the third reservoir at a fixed time interval.

60. The electrokinetic pump system of claim 55 further comprising a controller adapted to control delivery of power from the power source to the electrodes to move an amount dispensed fluid out of the third reservoir in response to a user input.

61. The electrokinetic pump system of claim 55 comprising:
    a first electrokinetic pump comprising the electrodes, the first, second and third reservoirs, the pump outlet, the dielectric material and the power source, the pump outlet comprising a first pump outlet, the first electrokinetic pump being adapted to move dispensed fluid into a patient through the first pump outlet;
    the system further comprising a second electrokinetic pump comprising a second pair of double-layer capacitive electrodes connectable to a power source, a porous dielectric disposed between the second pair of electrodes, a fourth reservoir containing pump fluid, a second reservoir and a sixth reservoir containing a dispensed fluid, and a second pump outlet, the second electrokinetic pump electrodes and dielectric material being adapted to move the second electrokinetic pump fluid out of the fourth reservoir into the fifth reservoir to move the second electrokinetic pump dispensed fluid through the second pump outlet into the patient when the second electrokinetic pump electrodes are connected to a power source substantially without the occurrence of Faradaic processes in the second pump,
    the system further comprising a controller adapted to control the first and second electrokinetic pumps.

62. The electrokinetic pump system of claim 61 wherein the first electrokinetic pump is further adapted move dispensed fluid at a first rate and the second electrokinetic pump is further adapted to move dispensed fluid at a second rate different than the first rate.

63. The electrokinetic pump system of claim 55 comprising:
a first electrokinetic pump comprising the electrodes, the first, second and third reservoirs, the pump outlet, the dielectric material and the power source, the first electrokinetic pump being adapted to move dispensed fluid into a patient;
the system further comprising a second electrokinetic pump comprising a pair of double-layer capacitive electrodes connectable to a power source, a porous dielectric disposed between the electrodes, a fourth reservoir containing pump fluid, a fifth reservoir and a sixth reservoir containing a dispensed fluid, the second electrokinetic pump electrodes and dielectric material being adapted to move the second electrokinetic pump fluid out of the fourth reservoir into the fifth reservoir to move the second electrokinetic pump dispensed fluid through the pump outlet into the patient when the second electrokinetic pump electrodes are connected to a power source substantially without the occurrence of Faradaic processes in the second pump.

64. The electrokinetic pump system of claim 63 wherein the first electrokinetic pump is further adapted move dispensed fluid at a first rate and the second electrokinetic pump is further adapted to move dispensed fluid at a second rate different than the first rate.

65. The electrokinetic pump system of claim 55 comprising:
a first electrokinetic pump comprising the electrodes, the first, second and third reservoirs, the pump outlet, the dielectric material and the power source, the first electrokinetic pump being adapted to move dispensed fluid into a patient;
the system further comprising a second electrokinetic pump comprising a pair of double-layer capacitive electrodes connectable to a power source, a porous dielectric disposed between the electrodes, a fourth reservoir containing pump fluid and a fifth reservoir, the second electrokinetic pump electrodes and dielectric material being adapted to move the second electrokinetic pump fluid out of the fourth reservoir into the fifth reservoir to move the dispensed fluid through the pump outlet into the patient when the second electrokinetic pump electrodes are connected to a power source substantially without the occurrence of Faradaic processes in the second pump.

66. The electrokinetic pump system of claim 55 further comprising a movable member disposed between the second reservoir and the third reservoir adapted to move as pump fluid moves from the first reservoir into the second reservoir to move the dispensed fluid out of the third reservoir.

67. The electrokinetic pump system of claim 66 wherein the movable member comprises a hydraulic amplifier.

68. The electrokinetic pump system of claim 55 further comprising a sensor adapted to determine a patient's need for the dispensed fluid.

69. The electrokinetic pump system of claim 68 further comprising a controller adapted to control delivery of power from the power source to the electrodes in response to a signal from the sensor.

70. The electrokinetic pump system of claim 68 wherein the sensor comprises an electrokinetic pump adapted to sample a fluid from the patient.

71. The electrokinetic pump system of claim 54 further comprising a third reservoir containing a sampled fluid and a pump inlet, the electrodes, dielectric material and power source being further adapted to move the sampled fluid into the pump inlet as the pump fluid moves from the first reservoir into the second reservoir.

72. The electrokinetic pump system of claim 71 further comprising a movable member disposed between the second reservoir and the first reservoir adapted to move as pump fluid moves from the first reservoir into the second reservoir to move the sampled fluid into the third reservoir.

73. The electrokinetic pump system of claim 54 further comprising a third reservoir, an external port communicating with the third reservoir and a movable member disposed between the second reservoir and the third reservoir adapted to change an effective volume of the third reservoir as an effective volume of the second reservoir changes.

74. The electrokinetic pump system of claim 73 further comprising a laminated housing, the electrokinetic pump system having a volume no greater than 250% of the largest effective volume of the third reservoir.

75. The electrokinetic pump system of claim 73 wherein the third reservoir comprises a syringe.

76. The electrokinetic pump system of claim 73 wherein the third reservoir comprises a collapsible container.

77. The electrokinetic pump system of claim 73 further comprising a sensor adapted to monitor a parameter related to an amount of fluid dispensed from the third reservoir.

78. The electrokinetic pump system of claim 77 further comprising a feedback control element adapted to control power delivered to the electrodes by the power source in response to a signal from the sensor.

79. The electrokinetic pump system of claim 78 wherein the parameter is flow rate of fluid dispensed from the third reservoir.

80. The electrokinetic pump system of claim 77 wherein the third reservoir comprises a syringe, the sensor being adapted to monitor a position of the syringe.

81. The electrokinetic pump system of claim 80 wherein the syringe comprises a plunger and a magnet, the sensor comprising a magnetostrictive sensor adapted to detect a position of the magnet.

82. The electrokinetic pump system of claim 80 further comprising a controller adapted to control application of power from the power source to the electrodes in response to a sensor output signal.

83. The electrokinetic pump system of claim 77 further comprising an indicator adapted to provide an indication related to fluid dispensed from the third reservoir.

84. The electrokinetic pump system of claim 83 wherein the indication comprises an occlusion of the external port.

85. The electrokinetic pump system of claim 52 wherein the electrodes, dielectric material and power source are further adapted to move substantially all of the pump fluid out of the reservoir substantially without the occurrence of Faradaic processes in the pump.

86. The electrokinetic pump system of claim 52 wherein the electrodes, dielectric material and power source are further adapted to move substantially all of the pump fluid out of the reservoir at a flow rate of less than about 1 microliter/minute and with a steady state flow rate error of no more than about 5% substantially without the occurrence of Faradaic processes in the pump.

87. The electrokinetic pump system of claim 52 wherein the electrodes, dielectric material and power source are further adapted to generate a pump fluid pressure between about 1 and about 1000 psi.

88. The electrokinetic pump system of claim 52 further comprising a housing having a volume of at most about 11 cm$^3$ and wherein the electrodes, dielectric material and power source are further adapted to move at least about 0.2 milliliters of pump fluid from the reservoir.

89. The electrokinetic pump system of claim 88 wherein the electrodes, dielectric material and power source are further adapted to move pump fluid from the reservoir at a rate of less than 10 nanoliters/min.

90. The electrokinetic pump system of claim 89 wherein the electrodes, dielectric material and power source are further adapted to move pump fluid from the reservoir from the reservoir substantially continuously for about 30 days.

91. The electrokinetic pump system of claim 88 wherein the housing comprises a laminated housing.

92. The electrokinetic pump system of claim 52 wherein the electrodes, dielectric material and power source are further adapted to be implanted in a patient.

93. The electrokinetic pump system of claim 52 further comprising an indicator adapted to indicate an amount of pump fluid present in the reservoir.

94. The electrokinetic pump system of claim 52 further comprising a controller adapted to provide power from the power source to the electrodes in a time modulated manner.

95. The electrokinetic pump system of claim 52 further comprising a controller adapted to alternate the power source between an on state and an off state.

96. The electrokinetic pump system of claim 52 further comprising a controller adapted to alternate the power source between a normally off state and a periodic on state in response to a computer program.

97. The electrokinetic pump system of claim 52 further comprising a housing containing the electrodes, reservoir, dielectric material and power source, the housing being adapted to be worn on a human or animal body.

98. A displacement pump comprising:
   a dispensed fluid reservoir;
   a pump outlet;
   a displacement mechanism;
   a power source adapted to operate the displacement mechanism; and
   a housing containing the reservoir, pump outlet, power source and displacement mechanism, the housing having a volume no more than 250% of the volume of the dispensed fluid reservoir;
   the displacement mechanism and power source being further adapted to dispense substantially all of dispensed fluid from the reservoir through the pump outlet at a flow rate no more than 1 microliter/minute with a steady state flow rate error of no more than about 5%.

99. The pump of claim 98 wherein the displacement mechanism comprises a movable member.

100. The pump of claim 99 wherein the displacement mechanism further comprises an electrokinetic assembly comprising a pair of electrodes connectable to the power source, a porous dielectric material disposed between the electrodes; and pump fluid in contact with the electrodes.

101. The pump of claim 100 wherein the electrodes comprise double-layer capacitive electrodes.

102. A pump comprising:
   a reservoir of pump fluid;
   a pump mechanism operable on the pump fluid;
   a pump outlet;
   a power source connectable to the pump mechanism to move pump fluid from the reservoir through the pump outlet at a flow rate no more than 1 microliter/minute with a steady state flow rate error of no more than about 5%; and
   a housing containing the reservoir, electrodes, pump outlet and power source, the housing having a volume no more than 150% of the volume of the reservoir.

103. The pump of claim 102 wherein the pump mechanism comprises a pair of double-layer capacitive electrodes having a capacitance of at least $10^{-2}$ Farads/cm$^2$.

* * * * *